United States Patent
Kim et al.

(10) Patent No.: US 12,298,214 B2
(45) Date of Patent: May 13, 2025

(54) DEVICE FOR WATER EXAMINATION

(71) Applicant: THE WAVE TALK, INC., Daejeon (KR)

(72) Inventors: Young Dug Kim, Seongnam-si (KR); Kyoung Man Cho, Seoul (KR)

(73) Assignee: THE WAVE TALK, INC., Daejeon (KR)

( * ) Notice: Subject to any disclaimer, the term of this patent is extended or adjusted under 35 U.S.C. 154(b) by 405 days.

(21) Appl. No.: 17/693,725

(22) Filed: Mar. 14, 2022

(65) Prior Publication Data
US 2022/0326132 A1 Oct. 13, 2022

(30) Foreign Application Priority Data

Apr. 8, 2021 (KR) .................. 10-2021-0045964

(51) Int. Cl.
*G01N 15/06* (2024.01)
*G01N 15/075* (2024.01)
(Continued)

(52) U.S. Cl.
CPC ......... *G01N 15/06* (2013.01); *G01N 21/4785* (2013.01); *G01N 21/4788* (2013.01);
(Continued)

(58) Field of Classification Search
CPC .............. G01N 15/06; G01N 21/4785; G01N 21/4788; G01N 15/075; G01N 2021/479; G01N 2021/516
See application file for complete search history.

(56) References Cited

U.S. PATENT DOCUMENTS 5,259,509 A * 11/1993 Boal, Jr. ............ B65D 21/0223
  206/508
5,854,685 A * 12/1998 Levine .................. G01J 3/1838
  356/439
(Continued)

FOREIGN PATENT DOCUMENTS

CN 103278472 A * 9/2013
CN 108474740 A 8/2018
(Continued)

OTHER PUBLICATIONS

Machine translation of WO-2019221557, 2024.*
(Continued)

*Primary Examiner* — Jonathan M Hansen
*Assistant Examiner* — Jarreas Underwood
(74) *Attorney, Agent, or Firm* — Kilpatrick Townsend & Stockton LLP

(57) ABSTRACT

Provided is a water examination device including: a main body; a fluid accommodation unit formed in the main body; a wave source for irradiating waves toward the fluid accommodation unit; a detector for detecting a laser speckle at every set time period that is set in advance, the laser speckle being generated due to multiple scattering of the waves in the fluid; a controller for estimating existence of impurities in the fluid in real-time by using the detected laser speckle; and a calibration unit for controlling the wave source or the detector such that an intensity of light irradiated from the wave source and measured by the detector is within a certain range set in advance.

16 Claims, 18 Drawing Sheets

(51) Int. Cl.
   *G01N 21/47*  (2006.01)
   *G01N 21/51*  (2006.01)

(52) U.S. Cl.
   CPC ..... *G01N 15/075* (2024.01); *G01N 2021/479* (2013.01); *G01N 2021/516* (2013.01)

(56) References Cited

U.S. PATENT DOCUMENTS

| | | | | |
|---|---|---|---|---|
| 5,923,372 | A * | 7/1999 | Han | H04N 23/72 |
| | | | | 348/363 |
| 6,041,020 | A * | 3/2000 | Caron | H04R 23/008 |
| | | | | 367/149 |
| 2003/0035155 | A1 * | 2/2003 | Chen | H04N 1/00005 |
| | | | | 358/504 |
| 2004/0070756 | A1 * | 4/2004 | Rastopov | G01N 15/0211 |
| | | | | 356/338 |
| 2008/0106737 | A1 * | 5/2008 | Weichselbaum | G01N 21/51 |
| | | | | 356/246 |
| 2011/0242523 | A1 | 10/2011 | Hall | |
| 2013/0245456 | A1 * | 9/2013 | Ferguson, Jr. | G06T 7/0012 |
| | | | | 600/407 |
| 2015/0116438 | A1 * | 4/2015 | Kim | G03G 15/5041 |
| | | | | 347/133 |
| 2016/0054294 | A1 * | 2/2016 | Rihani | G01N 21/0303 |
| | | | | 73/23.3 |
| 2016/0198961 | A1 * | 7/2016 | Homyk | A61B 5/681 |
| | | | | 600/476 |
| 2017/0209047 | A1 * | 7/2017 | Zalevsky | A61B 5/1455 |
| 2018/0372608 | A1 * | 12/2018 | Park | G01N 15/06 |
| 2020/0116618 | A1 * | 4/2020 | Park | G01N 15/06 |
| 2021/0025803 | A1 | 1/2021 | Kim et al. | |
| 2021/0080369 | A1 * | 3/2021 | Kim | G01N 33/487 |

FOREIGN PATENT DOCUMENTS

| | | | |
|---|---|---|---|
| CN | 112005099 A | | 11/2020 |
| KR | 10-2010-0137419 A | | 12/2010 |
| KR | 10-2015-0111538 A | | 10/2015 |
| KR | 10-2016-0030428 A | | 3/2016 |
| KR | 20180010589 A | | 1/2018 |
| KR | 20180040364 A | | 4/2018 |
| KR | 101939779 B1 | | 1/2019 |
| KR | 20200004128 A | * | 1/2020 |
| KR | 10-2020-0132357 A | | 11/2020 |
| WO | 2009/008745 A2 | | 1/2009 |
| WO | 2009/008745 A3 | | 1/2009 |
| WO | WO-2019221557 A1 | * | 11/2019 ............... A61L 2/28 |

OTHER PUBLICATIONS

Machine translation of KR-20200004128, 2024.*
Extended European Search Report for 22163115.3 mailed Aug. 10, 2022, 15 pages.
Yeo et al., "Optical Imaging and Analysis of Speckle Patterns from *Escherichia coli* in Disinfectant solution," Conference on Lasers and Electro-Optics-Europe, Technical Digest Series (Optica Publishing Group, 1998), paper <https://opg.optica.org/abstract.cfm?URI=CLEO_Europe-1998-CTul106>.
Office Action for CN 202210304784.1 mailed Sep. 26, 2024, 6 pages (English translation not provided).

* cited by examiner

FIG. 11A
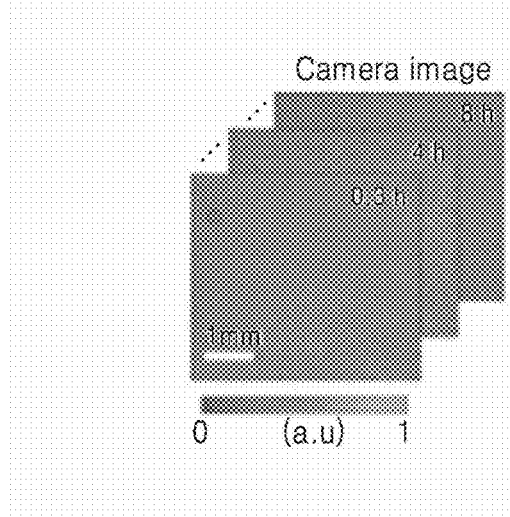
FIG. 11B
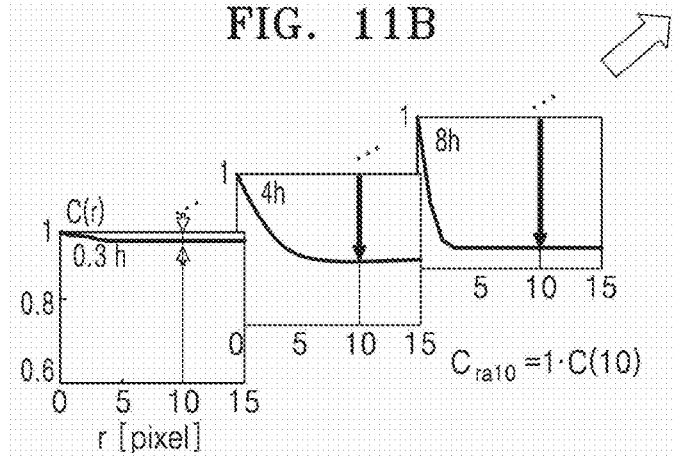
FIG. 11C
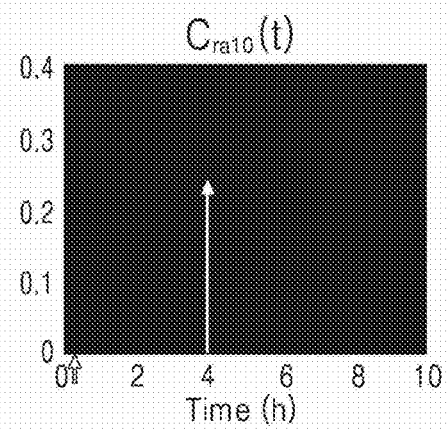
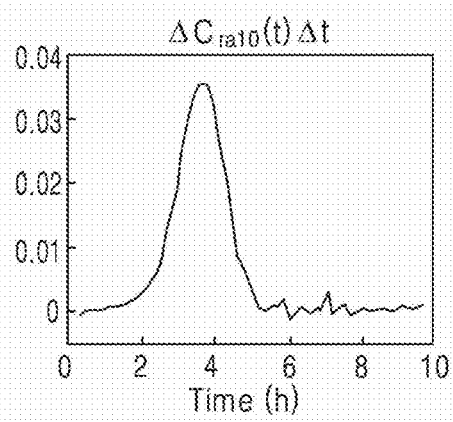

DEVICE FOR WATER EXAMINATION

CROSS-REFERENCE TO RELATED APPLICATIONS

This application is based on and claims priority under 35 U.S.C. § 119 to Korean Patent Application No. 10-2021-0045964 filed on Apr. 8, 2021, in the Korean Intellectual Property Office, the disclosure of which is incorporated by reference herein in its entirety.

BACKGROUND

1. Field

One or more embodiments of the present disclosure relate to a water examination device.

2. Description of the Related Art

In general, a fluid such as water or beverage is supplied to a user through various processes, e.g., filtration, etc. A fluid for drinking purposes has to be supplied to the user after materials, e.g., microbes, rather than additives that are added in the fluid according to necessity, are removed. However, during a process of treating the fluid, microbes in the fluid may unintentionally proliferate under a circumstance in which the fluid is in contact with external air.

Various methods have been suggested in order to examine water by sensing microbes in the fluid, but it is very difficult to sense a minimum amount of microbes in the fluid.

SUMMARY

The present disclosure provides a water examination device which examines water by sensing impurities including microbes in a fluid in real-time by using a chaotic wave sensor and a water monitoring system using the same.

Additional aspects will be set forth in part in the description which follows and, in part, will be apparent from the description, or may be learned by practice of the presented embodiments of the disclosure.

According to an embodiment of the present disclosure, a water examination device includes: a main body; a fluid accommodation unit formed in the main body; a wave source for irradiating waves toward the fluid accommodation unit; a detector for detecting a laser speckle at every set time period that is set in advance, the laser speckle being generated due to multiple scattering of the waves in the fluid; a controller for estimating existence of impurities in the fluid in real-time by using the detected laser speckle; and a calibration unit for controlling the wave source or the detector such that an intensity of light irradiated from the wave source and measured by the detector is within a certain range set in advance.

The detector may include a sensor unit and a shutter that is formed on one side of the sensor unit to block light incident in the sensor unit, and the calibration unit may control a shutter speed of the shutter.

Here, a calibration reference value of the calibration unit may be based on an average of intensity values of respective pixels in an image detected by the detector.

When the intensity of light detected by the detector is equal to or less than a first reference value, the calibration unit may control the shutter speed of the shutter to be decreased in order to increase the intensity of light incident in the sensor unit.

When the intensity of light detected by the detector is equal to or greater than a second reference value, the calibration unit may control the shutter speed of the shutter to be increased in order to decrease the intensity of light incident in the sensor unit.

When the intensity of light detected by the detector is equal to or less than the first reference value, the calibration unit may increase a voltage at the wave source in order to increase the intensity of light incident in the sensor unit.

When the intensity of light detected by the detector is equal to or greater than the second reference value, the calibration unit may decrease the voltage at the wave source in order to decrease the intensity of light incident in the sensor unit.

After calibrating the intensity of light detected by the detector within a certain range by the calibration unit, the controller may estimate whether there are impurities in the fluid by using the laser speckle.

The fluid accommodation unit may include: a bottom portion formed in the main body; and a wall portion formed to have a certain angle with respect to the bottom portion.

An angle between the bottom portion and the wall portion may not be a right angle.

The water examination device may further include: a water inlet pipe connected to the fluid accommodation unit to supply a fluid to the fluid accommodation unit; and a water outlet pipe connected to the fluid accommodation unit to discharge the fluid from the fluid accommodation unit to outside.

Dissolved oxygen may be removed from the fluid by regularly supplying the fluid to the fluid accommodation unit via the water inlet pipe and discharging the fluid from the fluid accommodation unit via the water outlet pipe.

The bottom portion or the wall portion may include a multiple scattering amplification region for amplifying the number of times of multiple scattering the wave irradiated from the wave source in the fluid.

The multiple scattering amplification region may amplify the number of times of multiple scattering the wave in the fluid by reflecting at least some of the wave irradiated from the fluid toward the fluid.

A temporal correlation of the detected laser speckle may be obtained by using the detected laser speckle, and existence of impurities in the fluid may be estimated in real-time based on the temporal correlation.

The temporal correlation may include a difference between first image information of the laser speckle detected at a first time point and second image information of the laser speckle detected at a second time point that is different from the first time point.

The first image information and the second image information may include at least one of pattern information of the laser speckle and intensity information of the wave.

The controller may obtain a spatial correlation of an interference pattern in an optical image detected by the detector and determine existence of impurities in the fluid based on a change in the spatial correlation of the interference pattern according to time.

According to another embodiment of the present disclosure, a water examination method includes: measuring, by a detector, an intensity of light irradiated from a wave source; determining, by a calibration unit, whether the intensity of light measured by the detector is equal to or greater than a first reference value; when the intensity of light measured by the detector is not equal to or greater than the first reference value, controlling, by the calibration unit, the intensity of light incident in the detector to be decreased; determining, by the calibration unit, whether the intensity of light measured by the detector is equal to or less than a second reference value; when the intensity of light measured by the detector is not equal to or less than the second reference value, controlling, by the calibration unit, the intensity of light incident in the detector to be increased; and estimating, by the controller, existence of impurities in the fluid by using a laser speckle detected by the detector in real-time.

When the intensity of light measured by the detector is equal to or less than the first reference value, the calibration unit may control the shutter speed of the shutter to be decreased in order to increase the intensity of light incident in the sensor unit.

When the intensity of light measured by the detector is equal to or less than the first reference value, the calibration unit may control the shutter speed of the shutter to be increased in order to decrease the intensity of light incident in the sensor unit.

Other aspects, features and advantages of the disclosure will become better understood through the accompanying drawings, the claims and the detailed description.

BRIEF DESCRIPTION OF THE DRAWINGS

The above and other aspects, features, and advantages of certain embodiments of the disclosure will be more apparent from the following description taken in conjunction with the accompanying drawings, in which:

FIGS. 10A-10D and 11A-11C are diagrams for describing principles of determining concentration information of high-concentration sample in a water examination device according to another embodiment of the present disclosure;

DETAILED DESCRIPTION

Figure 1:
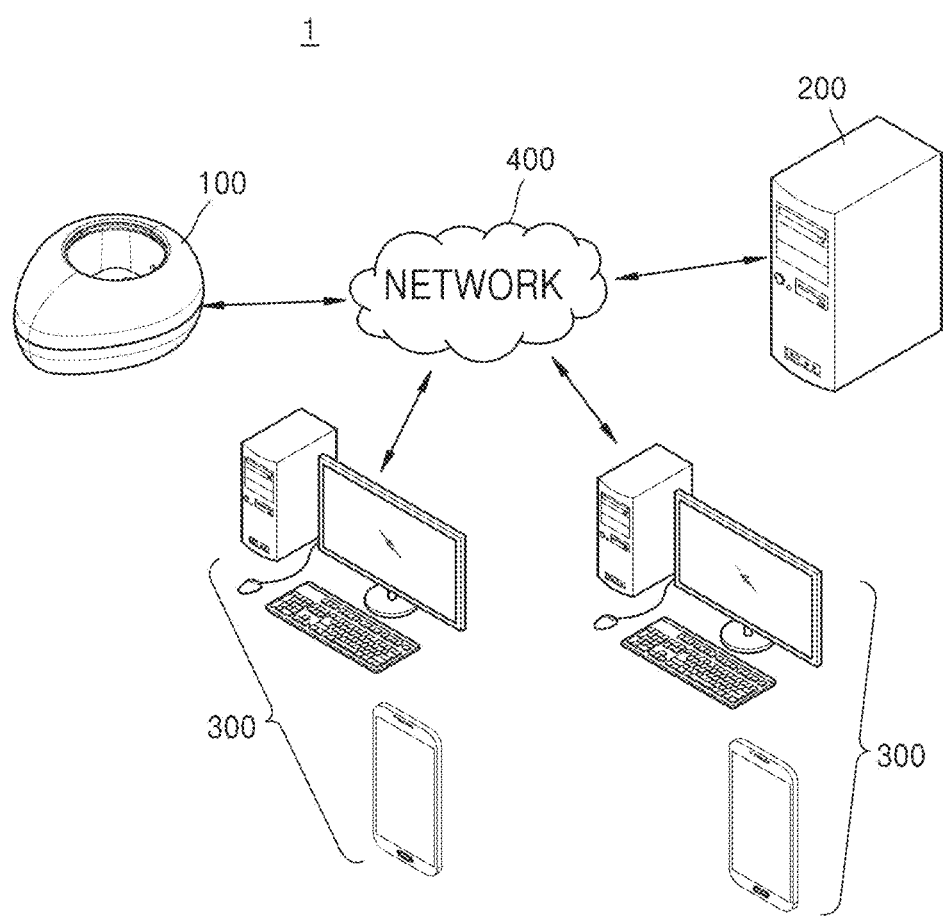
FIG. 1 is a conceptual diagram showing a water monitoring system according to an embodiment of the present disclosure.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects. As used herein, the term "and/or" includes any and all combinations of one or more of the associated listed items. Expressions such as "at least one of," when preceding a list of elements, modify the entire list of elements and do not modify the individual elements of the list.

The exemplary embodiments will be described below in more detail with reference to the accompanying drawings. Those components that are the same or are in correspondence are rendered the same reference numeral regardless of the figure number, and redundant explanations are omitted.

As the present disclosure allows for various changes and numerous embodiments, particular embodiments will be illustrated in the drawings and described in detail in the written description. The attached drawings for illustrating one or more embodiments are referred to in order to gain a sufficient understanding, the merits thereof, and the objectives accomplished by the implementation. However, the embodiments may have different forms and should not be construed as being limited to the descriptions set forth herein.

While such terms as "first," "second," etc., may be used to describe various components, such components must not be limited to the above terms. The above terms are used only to distinguish one component from another.

An expression used in the singular encompasses the expression of the plural, unless it has a clearly different meaning in the context.

In the present specification, it is to be understood that the terms such as "including," "having," and "comprising" are intended to indicate the existence of the features or components disclosed in the specification, and are not intended to preclude the possibility that one or more other features or components may exist or may be added.

It will be understood that when a unit, region, or component is referred to as being "formed on" another layer, region, or component, it can be directly or indirectly formed on the other layer, region, or component. That is, for example, intervening units, regions, or components may be present.

It will be understood that when an element is referred to as being "connected" or "coupled" to another element, it can be directly connected or coupled to the other element or intervening elements may be present.

It will be further understood that the terms "comprises," "comprising," "includes" and/or "including," when used herein, specify the presence of stated features or components, but do not preclude the presence or addition of one or more other features or components.

Sizes of components in the drawings may be exaggerated for convenience of explanation. In other words, since sizes and thicknesses of components in the drawings are arbitrarily illustrated for convenience of explanation, the following embodiments are not limited thereto.

FIG. 1 is a conceptual diagram showing a water monitoring system 1 according to an embodiment of the present disclosure.

Referring to FIG. 1, the water monitoring system 1 according to an embodiment of the present disclosure includes a water examination device 100, a server 200, and user terminals 300. In addition, the water monitoring system 1 also includes a network 400 connecting a plurality of water examination devices 100 and a plurality of user terminals 300 to the server 200.

The water examination device 100 according to an embodiment of the present disclosure examines the water by estimating whether there are impurities including microbes in a fluid and/or a concentration rapidly at low costs, according to a change in a temporal correlation or a spatial correlation of a laser speckle. The water examination device 100 according to an embodiment of the present disclosure will be described in detail below with reference to FIG. 2.

The server 200 according to an embodiment of the present disclosure collects water quality data examined by each water examination device 100, processes the water quality data, and provides the processed water quality data to the user terminals 300. FIG. 1 shows one server 200, but there may be a plurality of servers according to connection amount or data amount.

Here, the water quality data processed by the server 200 and provided to the user terminal 300 may include a water quality level measured by the corresponding user terminal 300 in comparison with a total water quality average, a water quality level in a region where the corresponding user terminal 300 is located in comparison with the total water quality average, a deviation in water quality according to the region, a variation in the water quality according to time, etc.

The plurality of user terminals 300 may denote communication terminals capable of using Web service in wired/wireless communication environment. Here, the user terminal 300 may include a personal computer of the user or a portable terminal of the user. Although a portable terminal is shown as a smartphone in FIG. 1, one or more embodiments of the present disclosure are not limited thereto, and any terminal having a display and a communicable application loaded thereon may be adopted without limitation.

In addition, the network 400 may connect the plurality of water examination devices 100, the plurality of user terminals 300, and the server 200. That is, the network 400 denotes a communication network for providing an access path, such that the water examination devices 100 and the user terminals 300 are connected to the server 200 and transmit/receive data therethrough. The above network 400 may support various near and far field communications such as Bluetooth, near field communication (NFC), ZigBee, Bluetooth, Wi-Fi, etc., as well as wired/wireless mobile communication networks and wired/wireless Internet.

Hereinafter, the water examination device 100 in the water monitoring system 1 according to an embodiment of the present disclosure will be described in detail below.

Figure 2:
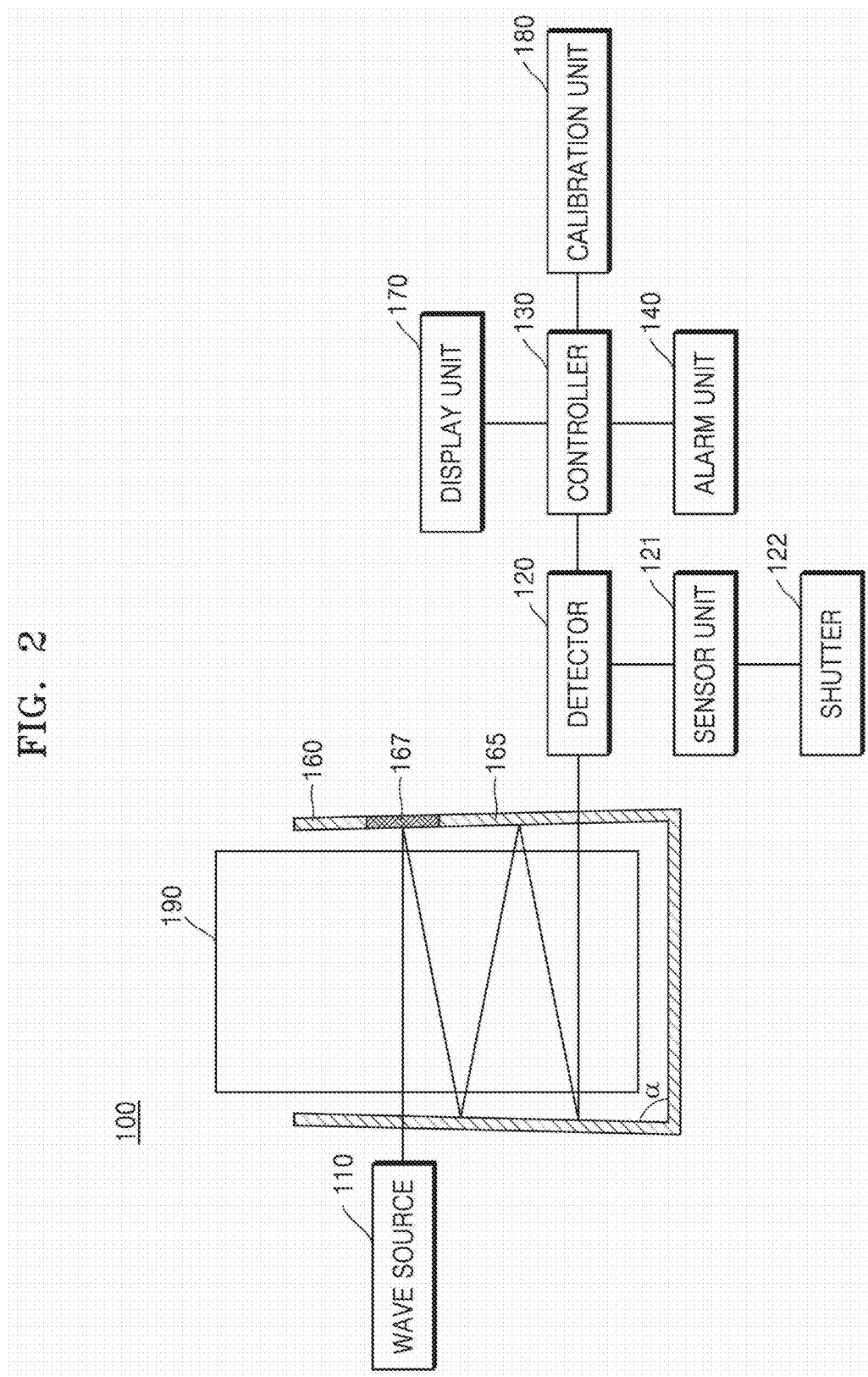
FIG. 2 is a conceptual diagram showing a water examination device in the water monitoring system of FIG. 1.
Figure 3:
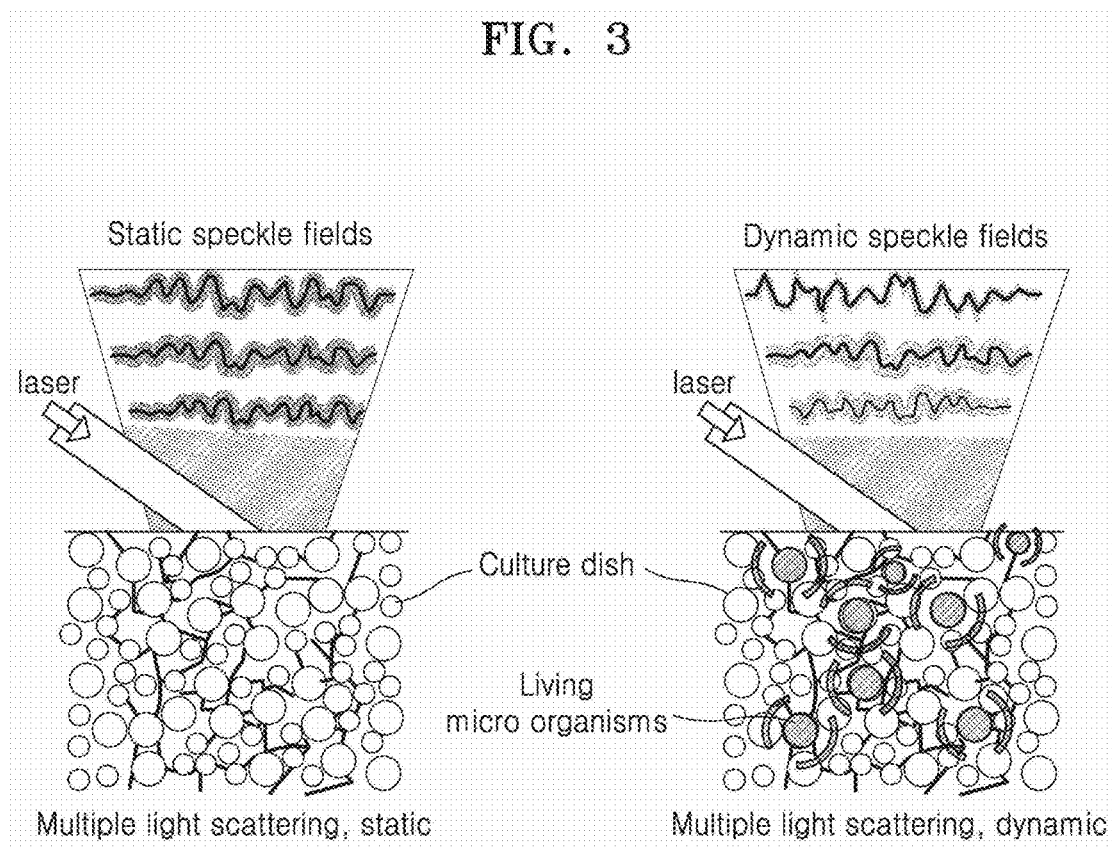
FIG. 3 is a diagram for describing principles of a chaotic wave sensor according to an embodiment of the present disclosure.
Figure 4:
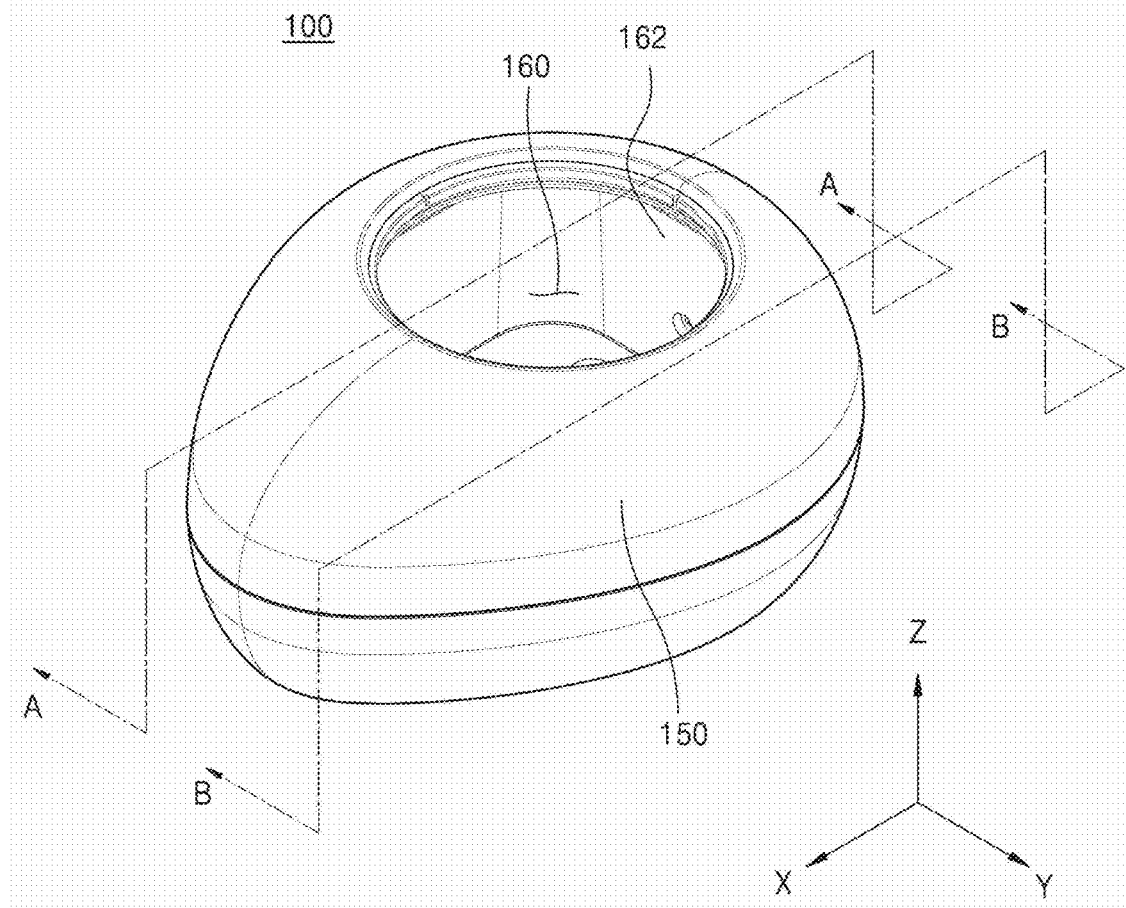
FIG. 4 is a perspective view of a water examination device actually implementing the conceptual diagram of FIG. 2.
Figure 5:
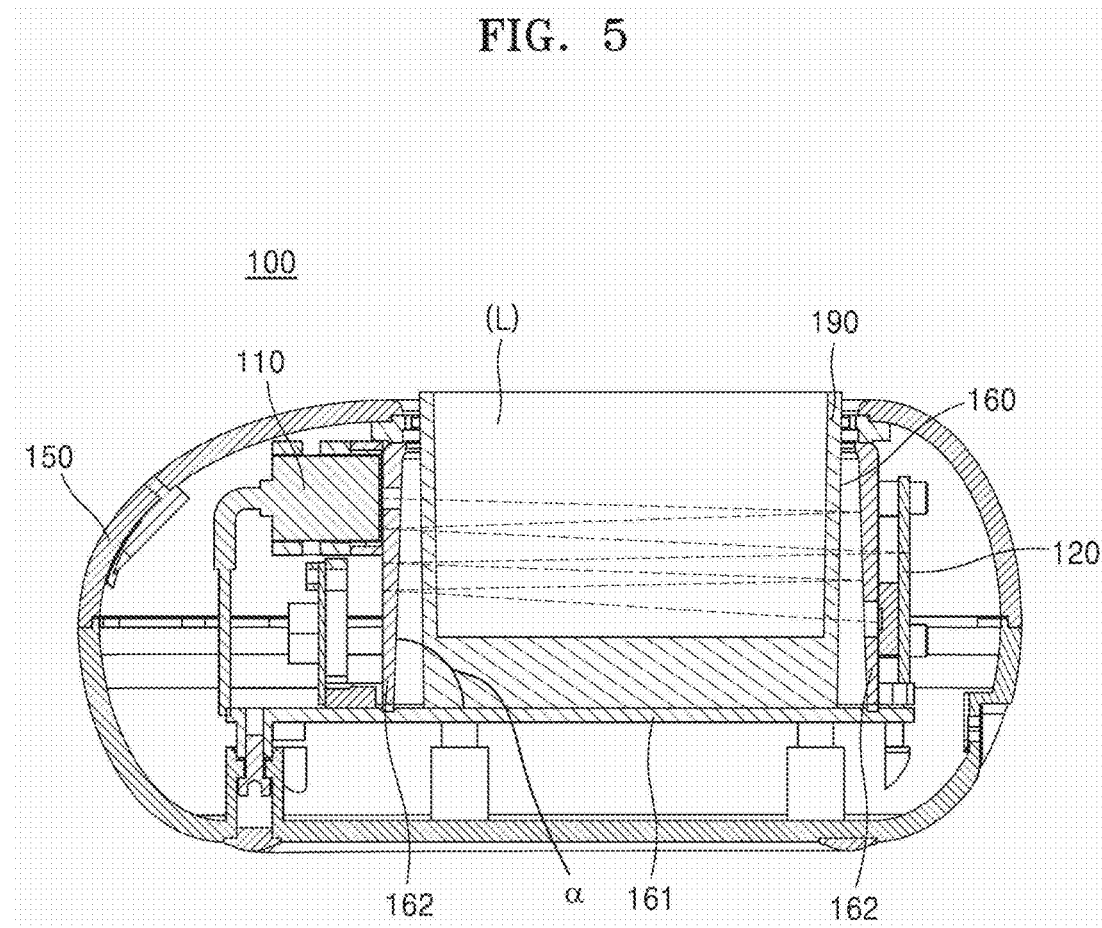
FIG. 5 is a cross-sectional view taken along line A-A of FIG. 4, and shows a state in which a cup is accommodated in a fluid accommodation unit.
Figure 6:
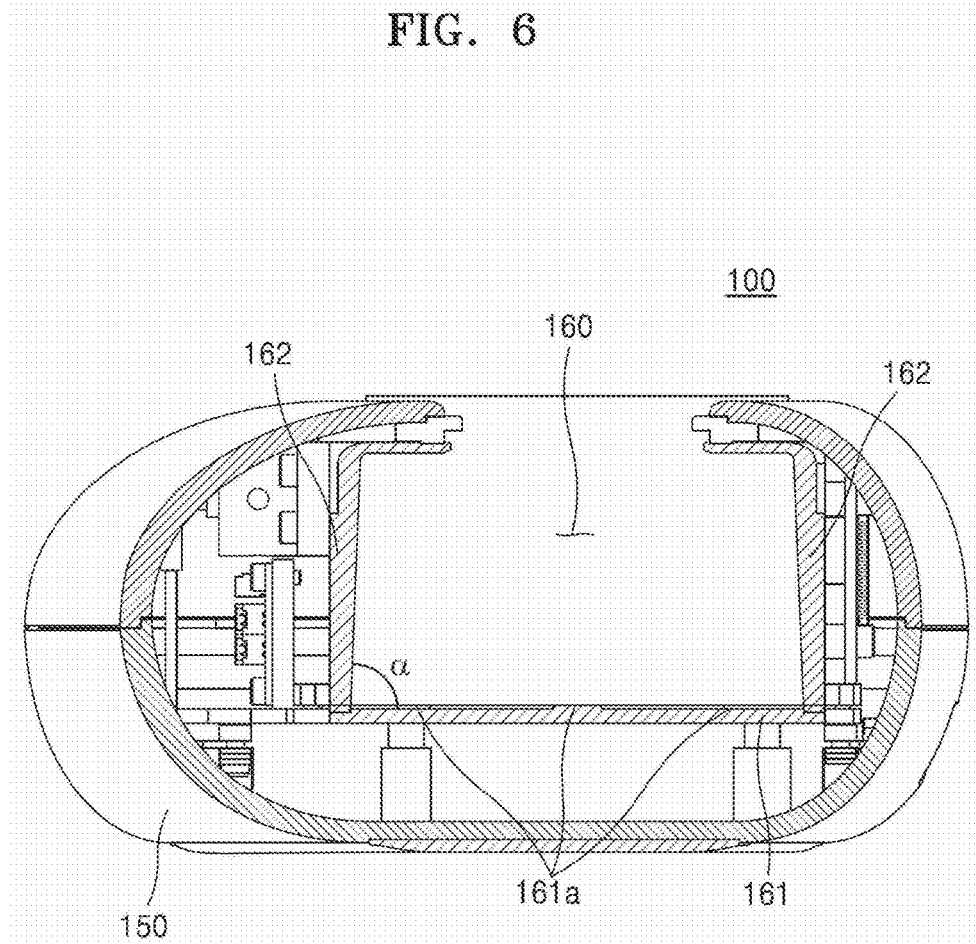
FIG. 6 is a cross-sectional view taken along line B-B of FIG. 4.
Figure 7:
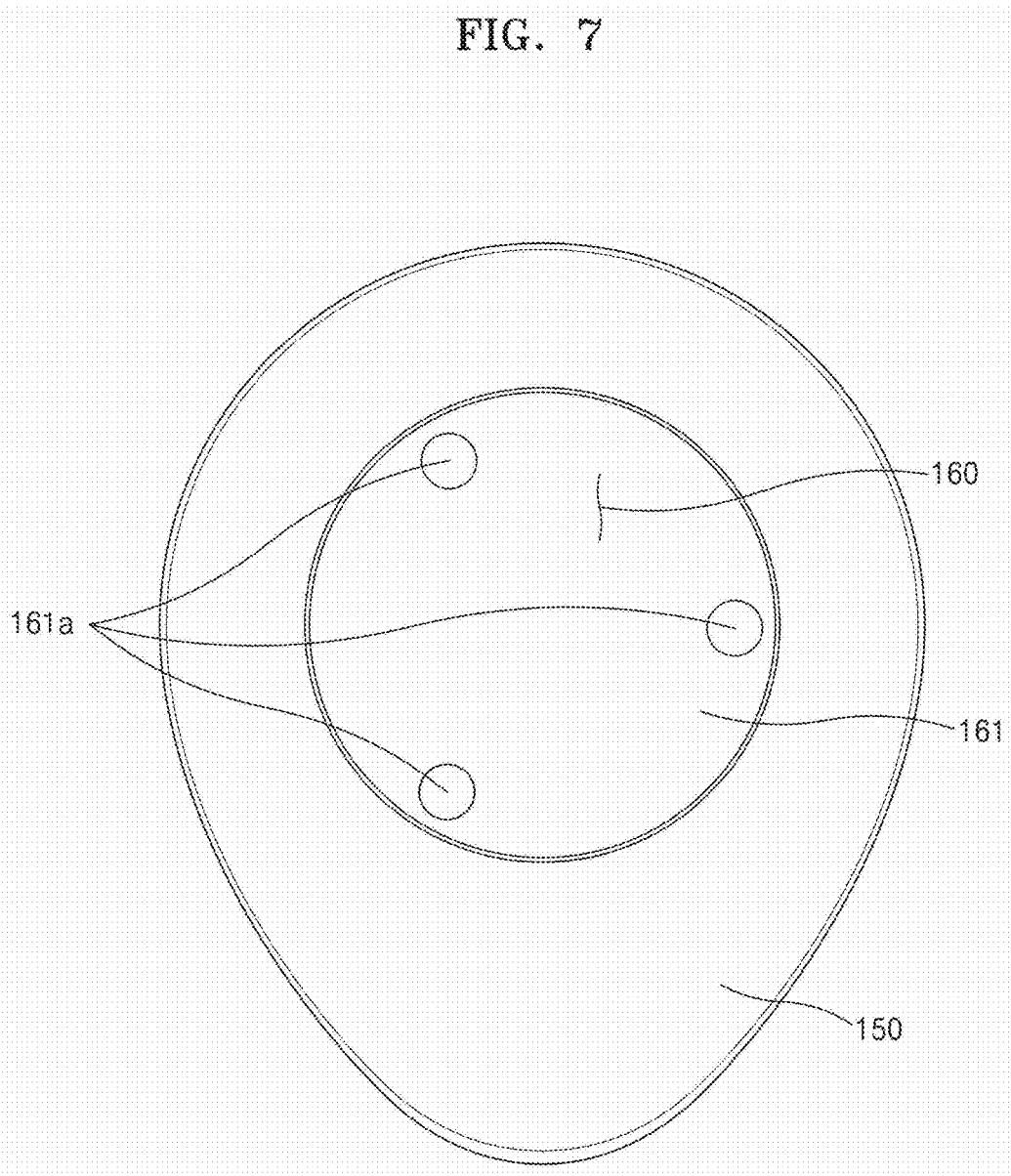
FIG. 7 is a plan view of the water examination device of FIG. 4.
Figure 8:
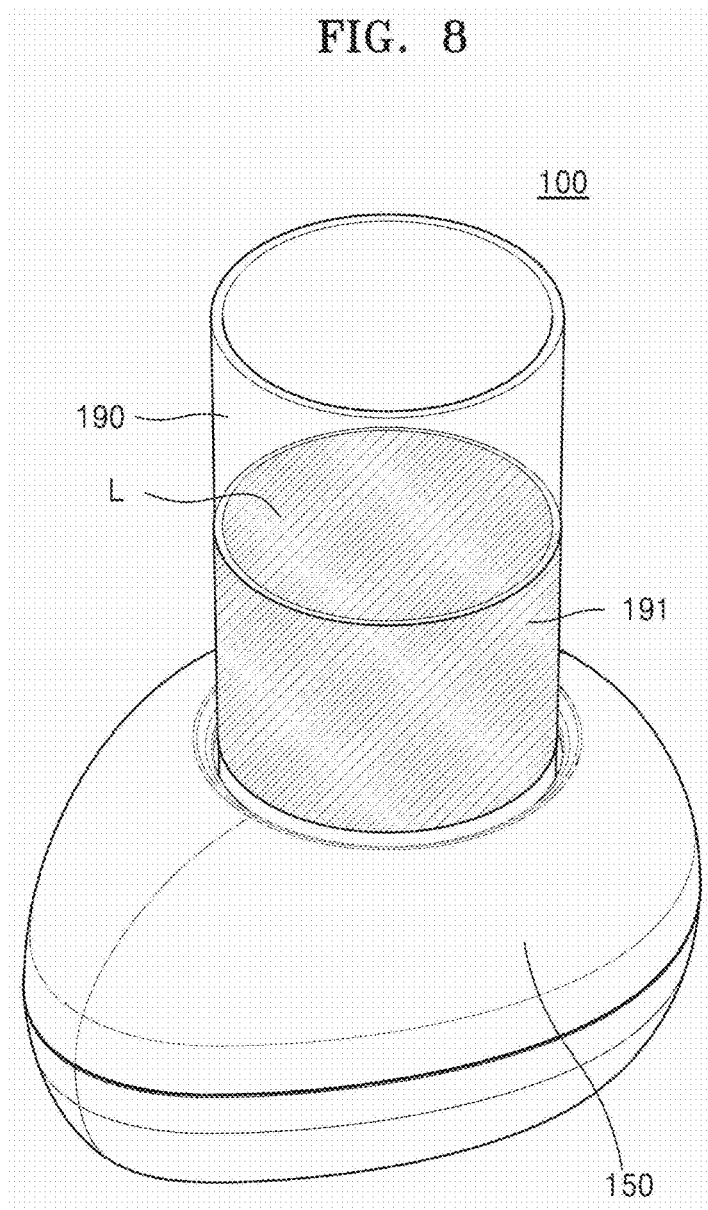
FIG. 8 is a perspective view showing a state in which a cup is installed in the fluid accommodation unit of FIG. 4.

FIG. 2 is a conceptual diagram of a water examination device 100 in the water monitoring system 1 of FIG. 1, and FIG. 3 is a diagram for describing a principle of a chaotic wave sensor according to an embodiment of the present disclosure. In addition, FIG. 4 is a perspective view of the water examination device 100 actually implementing the conceptual diagram of FIG. 2, and FIG. 5 is a cross-sectional view taken along line A-A of FIG. 4, and showing a state in which a cup 190 is accommodated in a fluid accommodation unit 160. FIG. 6 is a cross-sectional view taken along line B-B of FIG. 4, FIG. 7 is a plan view of the water examination device 100 of FIG. 4, and FIG. 8 is a perspective view showing a state in which a cup 190 is accommodated in the fluid accommodation unit 160 of FIG. 4.

Referring to FIG. 2, the water examination device 100 according to an embodiment of the present disclosure may include a wave source 110, a detector 120, and a controller 130. Also, the water examination device 100 of FIG. 2 may further include an alarm unit 140 and a fluid accommodation unit (see 160 of FIG. 5). In addition, the cup 190 containing a fluid L to be examined may be accommodated in the fluid accommodation unit 160. Also, the fluid accommodation unit 160 may include a multiple scattering amplification region 165 for amplifying the number of times of multiple scattering the wave irradiated from the wave source 110 in the fluid L. Also, the water examination device 100 of FIG. 2 may further include a display unit 170 and a calibration unit 180.

Here, the fluid L may include a liquid or a gas. Also, the fluid L may include a material in which microbes may proliferate, for example, water that does not contain a scattering material therein. However, one or more embodiments of the present disclosure are not limited thereto, and in another embodiment, the fluid L may include milk, etc. including a scattering material therein. Hereinafter, for convenience of description, an example in which the fluid L does not contain the scattering material will be described first, and an example in which the fluid L contains the scattering material will be described later.

The wave source 110 may irradiate a wave toward the fluid L in the cup 190 accommodated in the fluid accommodation unit 160. The wave source 110 may include all kinds of source devices capable of generating waves, for example, may be a laser irradiating light of a certain wavelength band.

The detector 120 may sense existence of microbes M, e.g., impurities in the fluid L by using the wave. In the present specification, the detector 120 may denote a chaotic wave sensor. Here, the impurities may include foreign matters that are non-soluble floating materials. The detector 120 may detect the foreign matters, as well as the microbes M, included in the fluid L. However, for convenience of description, an example in which the microbes M in the fluid L are detected will be described below.

Hereinafter, principles of a chaotic wave sensor according to an embodiment will be described with reference to FIG. 3.

When light is irradiated to a material having a uniform internal refractive index, e.g., glass, the light is refracted in a constant direction. However, when coherent light such as a laser is irradiated to a material having non-uniform internal refractive index, multiple scattering that is very complicated occurs in the material.

Referring to FIG. 3, in light or wave (hereinafter, referred to as wave for convenience' sake) irradiated from a wave source, some of the waves scattered through complicated paths due to the multiple scattering pass through a test target surface. Waves passing through multiple points in the test target surface generate constructive interference or destructive interference, and the constructive/destructive interference of the waves generates grain patterns (speckles).

In the present specification, the waves scattered in the complicated paths are referred to as "chaotic wave", and the chaotic wave may be detected through laser speckles.

A left side of FIG. 3 shows a state in which a laser is irradiated to a stabilized medium. When interference light (e.g., laser) is irradiated to the stabilized medium, in which internal component material does not move, a stabilized speckle pattern without a variation may be observed.

However, as shown at a right side of FIG. 3, when the medium having non-stabilized internal component that is moving, such as bacteria, the speckle pattern varies.

That is, the optical path may finely change according to time, due to fine activities of life (e.g., movement in cells, movement of microbes, and movement of ticks, etc.). Since the speckle pattern is generated due to interference of the waves, a fine change in the optical path may cause variation in the speckle pattern. Accordingly, when a temporal variation in the speckle pattern is measured, the activities of organisms may be rapidly measured. As described above, when the variation in the speckle pattern according to time is measured, existence of the organisms and concentration of the organisms may be identified, and further, kinds of the organisms may be identified.

In the present specification, a structure for measuring the variation in the speckle pattern is defined as a chaotic wave sensor.

In addition, because the fluid L such as water does not contain homogeneous materials that generate scattering therein as described above, the laser speckles may not be generated when the microbes M do not exist. However, the water examination device 100 according to an embodiment of the present disclosure may generate stabilized laser speckle pattern by multiple-scattering the waves via the multiple scattering amplification region 165 that will be described later. In the water examination device 100, the path of the waves may finely change due to the movement of the microbes when the microbes M exist in the fluid L contained in the cup 190. The fine change in the wave path may generate a change in the speckle pattern, and accordingly, the temporal change in the speckle pattern may be measured to rapidly detect whether there are the microbes M in the fluid L.

Referring back to FIG. 2 and FIG. 3, the water examination device 100 according to an embodiment of the present disclosure may include the wave source 110, the detector 120, and the controller 130.

The wave source 110 may irradiate the wave toward the fluid L in the cup 190 accommodated in the fluid accommodation unit 160. The wave source 110 may include all kinds of source devices capable of generating waves, for example, may be a laser irradiating light of a certain wavelength band. Although the present disclosure is not limited to the kind of wave source, for convenience of description, a case where the wave source is a laser will be described below.

For example, the laser having excellent coherence may be used as the wave source 110 in order to form speckles on the fluid L. Here, when a spectral bandwidth of the wave source is shorter, a measuring accuracy may increase, wherein the spectral bandwidth determines the coherence of the laser wave source. That is, when a coherence length increases, the measuring accuracy also increases. Accordingly, a wave source irradiating the laser having a spectral bandwidth that is less than a reference bandwidth set in advance may only be used as the wave source 110, and the shorter the spectral bandwidth is as compared with the reference bandwidth, the higher the measuring accuracy is. For example, the spectral bandwidth of the wave source may be set to satisfy following condition of Equation 1 below.

$$\text{Spectral bandwidth} < 1 \text{ nm} \qquad \text{[Equation 1]}$$

According to Equation 1 above, when the light is irradiated into the fluid at every reference time in order to measure a variation in the laser speckle pattern, the spectral bandwidth of the wave source 110 may be maintained to be less than 1 nm.

The detector 120 may detect the laser speckles that are generated when the irradiated waves are multiple scattered in the fluid L, at every preset time point. Here, the time point may denote one instant during continuous flow of time, and time points may be set in advance with constant time intervals therebetween, but are not limited thereto, that is, may be set in advance with an arbitrary time interval. The detector 120 may include a sensing unit corresponding to the kind of the wave source 110, for example, a CCD camera that is an imaging device in a case where a light source of a visible ray wavelength band is used. The detector 120 may detect the laser speckle at a first time point at least, and may detect the laser speckle at a second time point, and then, may provide the controller 130 with the detected laser speckles. The first time point and the second time point are just examples selected for convenience of description, and the detector 120 may detect laser speckles at a plurality of time points more than the first and second time points.

In detail, when the wave is irradiated to the fluid L, the incident wave may generate laser speckle due to the multiple scattering. The laser speckle is generated by light interference effect, and thus, when there are no microbes in the fluid L, a constant interference pattern may be shown according to time due to the multiple scattering amplification region. Comparing with this, when microbes exist in the fluid L, the laser speckle may vary according to time due to the movement of the microbes M. The detector 120 detects the laser speckle varying according to the time at every time point set in advance, to provide the laser speckle to the controller 130. The detector 120 may detect the laser speckle at a sufficient speed to sense the movement of the microbes M, for example, 25 frames to 30 frames per second.

In addition, when the image sensor is used as the detector 120, the image sensor may be arranged so that a size d of one pixel in the image sensor is equal to or less than a grain size of the speckle pattern. For example, the image sensor may be arranged in the optical system included in the detector 120, to satisfy the condition of Equation 2 below.

$$d \leq \text{speckle grain size} \qquad \text{[Equation 2]}$$

As expressed by Equation 2 above, the size d of one pixel in the image sensor has to be equal to or less than the grain size of the speckle pattern, but the size of the pixel is too small, an undersampling may occur and it may be difficult to utilize the pixel resolution. Accordingly, in order to achieve an effective signal to noise ratio (SNR), the image sensor may be arranged to make five or less pixels correspond to the speckle grain size.

The controller 130 may obtain a temporal correlation of the detected laser speckle, by using the detected laser speckle. The controller 130 may estimate whether the microbes exist in the fluid L in real-time based on the obtained temporal correlation. In the present specification, real-time denotes estimating whether microbes M exist within 3 seconds, for example, the existence of the microbes M may be estimated within one second.

In an embodiment, the controller 130 may estimate whether the microbes exist by using a difference between first image information of the laser speckle detected at a first time point and second image information of the laser speckle detected at a second time point that is different from the first time point. Here, the first image information and the second image information may include at least one of laser speckle pattern information and wave intensity information.

In addition, according to the embodiment, the difference between the first image information at the first time point and the second image information at the second time point is not only used, but image information of a plurality of laser speckles at a plurality of time points may be also used. The controller 130 may calculate a temporal correlation coefficient between the images by using image information of the laser speckles generated at the plurality of time points set in advance, and may estimate existence of the microbes M in the fluid L based on the time correlation coefficient. The temporal correlation coefficient between the detected laser speckle images may be calculated by using Equation 3 below.

$$\bar{C}(x, y; \tau) = \frac{1}{T-\tau} \sum_{t=1}^{T-\tau} \bar{I}(x, y; t) \bar{I}(x, y; t+\tau) \delta t \quad \text{[Equation 3]}$$

In Equation 3 above, $\bar{C}$ denotes a temporal correlation coefficient, $\bar{I}$ denotes a standardized light intensity, (x,y) denotes a pixel coordinate, t denotes a measured time, T denotes a total measured time, and $\tau$ denotes a time lag.

According to Equation 3, the temporal correlation coefficient may be calculated, and as an embodiment, the existence of the microbes may be estimated by analyzing whether the temporal correlation coefficient is below a reference value set in advance. In detail, when the temporal correlation coefficient is below the reference value beyond an error range set in advance, it may be estimated that the microbes exist.

In addition, the detector 120 may estimate the concentration of impurities in the fluid L contained in the cup 190. Here, the detector 120 may perform a function of measuring a turbidity of the fluid L by estimating the concentration of the impurities in the fluid L. It is difficult to measure the impurity concentration of 105 cfu/ml or less by using a general turbidity measuring device. However, the detector 120 according to an embodiment of the present disclosure may measure the impurity concentration of 106 cfu/ml or less through a method of determining the impurity concentration as described below. Here, the impurities are not limited to the microbes. Hereinafter, for convenience of description, a method of determining the concentration of the microbes by using the laser speckles in the controller 130 will be described based on an example in which the impurities are microbes.

The controller 130 may calculate a standard deviation of light intensity of the laser speckle, with respect to a laser speckle image captured at every reference time. As the microbes existing in the fluid L continuously move, constructive interference and destructive interference may vary according to the movements. Here, when the constructive interference and the destructive interference change, the light intensity may largely change. Then, the controller 130 may calculate the standard deviation representing the variation degree of the light intensity, to detect the microbes in the cup 190 and measure a distribution degree of the microbes.

For example, the controller 130 combines the laser speckle images that are measured at every time point determined in advance, and may calculate the standard deviation of the light intensity of the laser speckle according to time in the combined images. The standard deviation of the light intensity of the laser speckle according to time may be calculated by using Equation 4 below.

$$S(x, y) = \sqrt{\frac{1}{T} \sum_{t=1}^{T} (I_t(x, y) - \bar{I})^2} \quad \text{[Equation 4]}$$

In Equation 4 above, S denotes the standard deviation, (x,y) denotes a pixel coordinate of the camera, T denotes a total measurement time, t denotes a measurement time, $I_t$ denotes a light intensity measured at the time t, and $\bar{I}$ denotes an average light intensity according to time.

The constructive and destructive interferences may vary depending on the movements of the microbes, and the standard deviation value calculated according to the Equation 4 increases. Thus, the concentration of the microbes may be measured based on the standard deviation value. However, one or more embodiments of the present disclosure are not limited to the method of measuring the concentration of microbes by using Equation 4 above, and the concentration of microbes may be measured by any method provided that the method uses the difference in the detected laser speckles.

In addition, the controller 130 may measure distribution, that is, concentration of the microbes included in the fluid, based on a linear relationship between a magnitude of the standard deviation value of the laser speckle light intensity and the concentration of the microbes.

In addition, the multiple scattering amplification region 165 may reflect at least some of the waves emitted from the fluid L into the fluid L again, in order to amplify the number of multiple scattering times in the fluid L. The multiple scattering amplification region 165 may include a multiple scattering material. For example, the multiple scattering material may include particles each having a diameter equal to or less than a micrometer and having a large refractive index, for example, titanium oxide (TiO$_2$) nano-particles. Here, the multiple scattering amplification region 165 may be formed by coating the multiple scattering material onto surfaces of a bottom portion (see 161 of FIG. 5) and a wall portion (see 163 of FIG. 5) of the fluid accommodation unit 160. However, one or more embodiments are not limited thereto, and in another embodiment, the bottom portion (see 161 of FIG. 5) and the wall portion (see 163 of FIG. 5) may include the multiple scattering material to form the multiple scattering amplification region 165.

In addition, at least part of the multiple scattering amplification region 165 may include a reflective region 167 that reflects all of the waves emitted from the fluid L onto the fluid L. The reflective region 167 may minimize emitting of the waves from the fluid L to outside the water examination device 100, and a microbe sensing rate of the detector 120 may be amplified. The reflective region 167 may be arranged to face an incident region in which the waves from the wave source 110 are incident. The reflective region 167 reflects all of the waves irradiated from the wave source 110 into the fluid L, and thus, the wave amount that may be multiple scattered in the fluid L may be increased, thereby amplifying the microbes sensitivity of the detector 120. In another embodiment, the entire area of the multiple scattering amplification region 165, except for the moving path of the waves emitted to the detector 120, may include a reflective region.

Referring back to FIG. 2, the water examination device 100 according to an embodiment of the present disclosure may further include the alarm unit 140 and the display unit 170. In addition, the water examination device 100 may be connected to the external user terminal 300 (see FIG. 1) or the server 200 (see FIG. 1) via the network 400 (see FIG. 1).

When a signal t1 representing that there are microbes is input from the controller 130, the alarm unit 140 may notify the user. The alarm unit 140 may notify that there are microbes in the fluid by using any one of sound and light. The alarm unit 140 may include an illumination unit such as an LED generating an alarm signal via light and a speaker (not shown) generating an alarm signal via sound, and the light and the sound may be simultaneously generated.

Also, the water examination device 100 may further include a communication unit (not shown) for communicating with the user terminal 300 (see FIG. 1). When the signal t1 representing that there are the microbes is input from the controller 130, the alarm unit 140 may provide the user terminal 300 (see FIG. 1) with the information including a microbe sensing signal via a wired or wireless communication unit (not shown). Also, the alarm unit 140 may provide the server 200 (see FIG. 1) with the above information. When information about whether to sense the microbes, the time of sensing the microbes, and the concentration of the microbes is uploaded through the alarm unit 140, the water examination device 100 registers the information on the server 300 (see FIG. 1) and provides an interface for allowing other users to search for data registered on the server 300 (see FIG. 1). The water examination device 100 according to an embodiment may establish a database including microbes generation situation, etc. through the above processes. The user terminal 300 (see FIG. 1) may include a personal computer or a portable terminal through which Web service may be used in wired/wireless communication environment.

The display unit 170 outputs a detecting result from the detector 120 as visual information. That is, various data may be output by processing information on existence of the microbes in the fluid L and/or concentration of the microbes, and turbidity information in the fluid estimated therefrom, etc. Here, image treatment processes for outputting received image as an image through the display unit 170 may be performed by the controller 130.

Here, the water examination device 100 of the water monitoring system 1 according to an embodiment of the present disclosure may further include the calibration unit 180.

The calibration unit 180 controls the water examination device 100 such that the intensity of light irradiated from the wave source 110 and measured by the detector 120 after passing through the multiple scattering amplification region 165 may be within a certain range set in advance.

Here, according to an embodiment of the present disclosure, the calibration unit 180 may control a shutter speed of the detector 120 such that the intensity of light measured by the detector 120 may be within a certain range set in advance. This will be described below in more detail.

The detector 120 is formed similarly to a camera and may detect the light that is irradiated from the wave source 110 and passes through the multiple scattering amplification region 165. The detector 120 may include a sensor unit 121 including an image sensor and a shutter 122. Basically, when the shutter 122 is opened, the light is incident in the sensor unit 121, and when the shutter 122 is closed, the light incident in the sensor unit 121 is blocked. Here, the shutter speed denotes a speed of opening and closing the shutter 122, and when the shutter speed is slow, the intensity of light incident in the sensor unit 121 increases, and when the shutter speed is fast, the intensity of light incident in the sensor unit 121 decreases.

Here, a calibration reference value may be determined from an average of intensity values of respective pixels in an image detected by the detector 120.

In detail, in case of an 8-bits image sensor, an intensity of each pixel has a value between 0 to 255, and an intermediate value, that is, 128, may be set as a reference value. In addition, based on various experimental data, an appropriate light intensity range may be set as ±5 from the reference value. In addition, a minimum value of the appropriate light intensity range is set as a first reference value and a maximum value of the appropriate light intensity range may be set as a second reference value.

For example, when the average value of the intensities ranges from 123 to 133, it may be set as an appropriate light intensity. (Here, the first reference value may be 123 and the second reference value may be 133.) In addition, an average of the intensity values of the pixels in the image that is irradiated from the wave source 110 and detected by the detector 120 after passing through the multiple scattering amplification region 165 is measured, and when the average of the intensity values is less than 123, the calibration unit 180 determines that the light intensity is not sufficient and may decrease the shutter speed in order to increase the intensity of light incident in the sensor unit 121. On the contrary, when the average of the intensity values of the pixels in the detected image is greater than 133, the calibration unit 180 determines that the light intensity is excessive and may increase the shutter speed in order to decrease the intensity of the light incident in the sensor unit 121.

As described above, because the intensity of light detected by the detector 120 is calibrated within a certain rage by the calibration unit 180, a consistent reference value may be set with respect to the intensities of the light measured from a plurality of water examination devices 100 located at different positions.

As described above, after calibrating the intensity of light detected by the detector 120 within a certain range by using the calibration unit 180, the controller 130 may obtain the temporal correlation of the laser speckle. Thus, even when the performance of the wave source 110 degrades or there is a deviation in container containing the fluid sample, an error in obtaining the temporal correlation of the laser speckle may be minimized.

A method of performing the water quality monitoring by using the water monitoring system 1 according to an embodiment of the present disclosure will be described below with reference to FIGS. 12 and 13.

In addition, according to another embodiment of the present disclosure, the calibration unit 180 controls the intensity of light irradiated from the wave source 110 itself, in order to set the intensity of light measured by the detector 120 within a certain range.

That is, an average of the intensity values of the pixels in the image that is irradiated from the wave source 110 and detected by the detector 120 after passing through the multiple scattering amplification region 165 is measured, and when the average of the intensity values is less than 123, the calibration unit 180 determines that the light intensity is not sufficient and may increase the intensity of light irradiated from the wave source 110 by increasing the voltage of the wave source 110 in order to increase the intensity of the light incident in the sensor unit 121. On the contrary, when the average of the intensity values of the pixels in the detected image is greater than 133, the calibration unit 180 determines that the light intensity is excessive and may decrease the intensity of light irradiated from the wave source 110 by decreasing the voltage of the wave source 110 in order to decrease the intensity of the light incident in the sensor unit 121.

Referring to FIGS. 4 to 8, the water examination device 100 according to an embodiment of the present disclosure may include the wave source 110, the detector 120, a main body 150, and the fluid accommodation unit 160. Also, although not shown in FIGS. 4 to 8, the water examination device 100 may further include the controller 130 (see FIG. 2) and the alarm unit 140 (see FIG. 2) described above with reference to FIG. 2. Here, the wave source 110 and the detector 120 are described above with reference to FIG. 2, and detailed descriptions thereof are omitted.

The main body 150 forms an outer appearance of the water examination device 100, and may include the wave source 110, the detector 120, and the fluid accommodation unit 160 formed therein. In the drawings, the main body 150 is formed as an eccentric streamlined shape (or an egg shape when seen from above), and the fluid accommodation unit 160 in which the cup 190 may be inserted is formed inward from an upper portion thereof. However, one or more embodiments are not limited thereto, and a size, a shape, or a material of the main body 150 or a position in the main body 150 where the fluid accommodation unit 160 is formed may be variously changed. Here, the fluid accommodation unit 160 may function as a cup accommodation unit in which the cup 190 may be accommodated.

The fluid accommodation unit 160 may be formed such that the cup 190 may be inserted to inside (that is, toward the center portion) from the upper portion of the main body 150. The fluid accommodation unit 160 may include the bottom portion 161 and the wall portion 162. In other words, it may be expressed that the bottom portion 161 and the wall portion 162 may form the fluid accommodation unit 160 in which the cup 190 may be accommodated and seated.

The bottom portion 161 forms a bottom surface of the fluid accommodation unit 160 and has a flat surface. The bottom portion 161 may at least partially include the multiple scattering amplification region 165 described above.

Here, the water examination device 100 according to an embodiment of the present disclosure include three or more support portions 161*a* protruding from the bottom portion 161 so as to stably support the cup 190 that is accommodated in the fluid accommodation unit 160.

In detail, the cup 190 for containing the fluid has various shapes, and may not have a flat bottom surface. In this case, when the cup 190 is seated in the fluid accommodation unit 160, the cup 190 may not be stabilized, but finely shakes such that an error may occur in the measured value.

To address the above issue, according to an embodiment of the present disclosure, the three or more support portions 161*a* protrude from the bottom portion 161 and stably support the cup 190 accommodated in the fluid accommodation unit 160.

As described above, when three or more support portions 161*a* protrude from the bottom portion 161, the bottom portion 161 and the bottom surface of the cup 190 are in three-point (or more) contact with each other, not in the surface contact with each other. Through the three-point contact, fine shaking that may occur when the bottom surface of the cup 190 is not flat may be minimized, and an accuracy during repeated measurements may be improved.

In addition, the wall portion 162 is formed in an approximately perpendicular direction from the bottom portion 161, and has a loop shape such that the cup 190 may be accommodated therein. The multiple scattering amplification region 165 and/or the reflective region 167 described above may be formed in at least a part of the wall portion 162.

Here, in the water examination device 100 according to an embodiment of the present disclosure, an angle (a) between the wall portion 162 and the bottom portion 161 is not a right angle, but is slightly inclined (that is, oblique).

In detail, the water examination device 100 according to an embodiment of the present disclosure has a structure, in which the portion where the fluid accommodation unit 160 is formed is opened to accommodate the cup 190. When the light is scattered due to the reflection of laser in the above structure in which one surface (of which at least a part) is opened, the scattered light is partially emitted out of the opened structure, and thus, there is a loss of the light intensity received by the detector 120 (see FIG. 2), which affects a result obtained through the light scattering analysis.

To address the above issue, according to one embodiment of the present disclosure, the angle ($\alpha$) formed by the wall portion 162 and the bottom portion 161 is not the right angle, but is slightly inclined. That is, the wall portion 162 is formed such that the angle ($\alpha$) formed by the wall portion 162 and the bottom portion 161 is about 85° to 88°, and thus, the laser reflected by the wall portion 162 proceeds toward a side opposite to the opened surface to reduce the loss of light intensity. Therefore, the light scattering effect may be improved.

In other words, the wall portion 162 may be formed to have a narrowed entrance in an upward direction (that is, in a +z direction), or may have a diameter that is gradually reduced upward. According to the present disclosure, the loss of light emitted from the wave source 110 is reduced, and the light scattering effect may be improved.

In addition, the cup 190 may include an opaque portion 191. In detail, when the cup 190 is formed to be entirely transparent, the laser may be exposed to outside, and the user may feel glaring effect. Also, there is a need to indicate an amount of minimum fluid that is necessary for examining the quality of fluid in the cup 190 by using the water examination device 100.

In order to address the above issue, the opaque portion 191 is formed in at least a part of the cup 190, in particular, to a certain height at a side lower portion of the cup 190, such that the minimum flow amount that is necessary for examining the fluid quality is indicated to the user, and at the same time, the user may not directly see the laser with naked eyes.

Figure 9A:
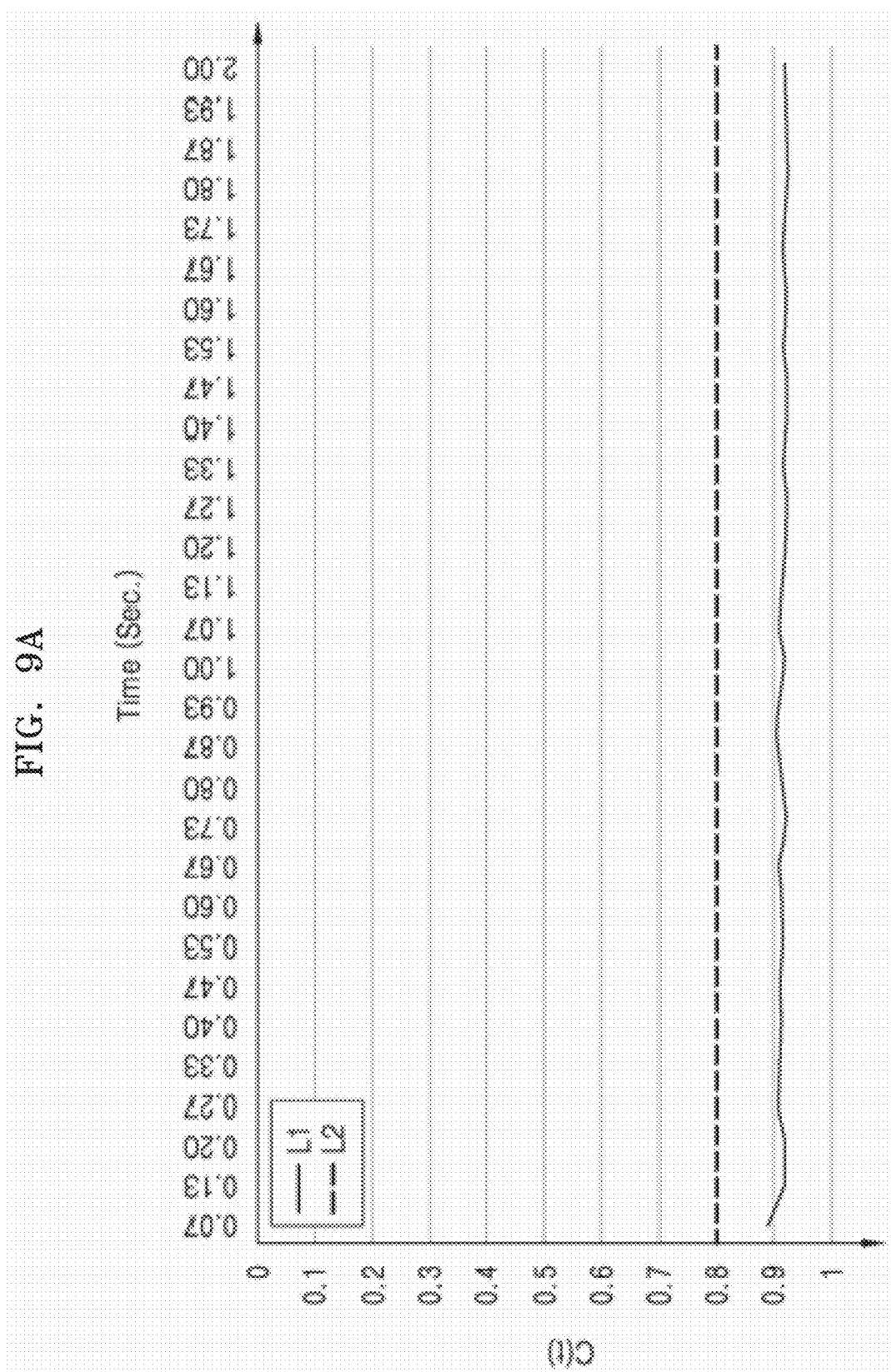
FIGS. 9A to 9C are graphs showing a temporal correlation coefficient according to a bacterial concentration in a fluid in a water examination device according to an embodiment of the present disclosure.
Figure 9B:
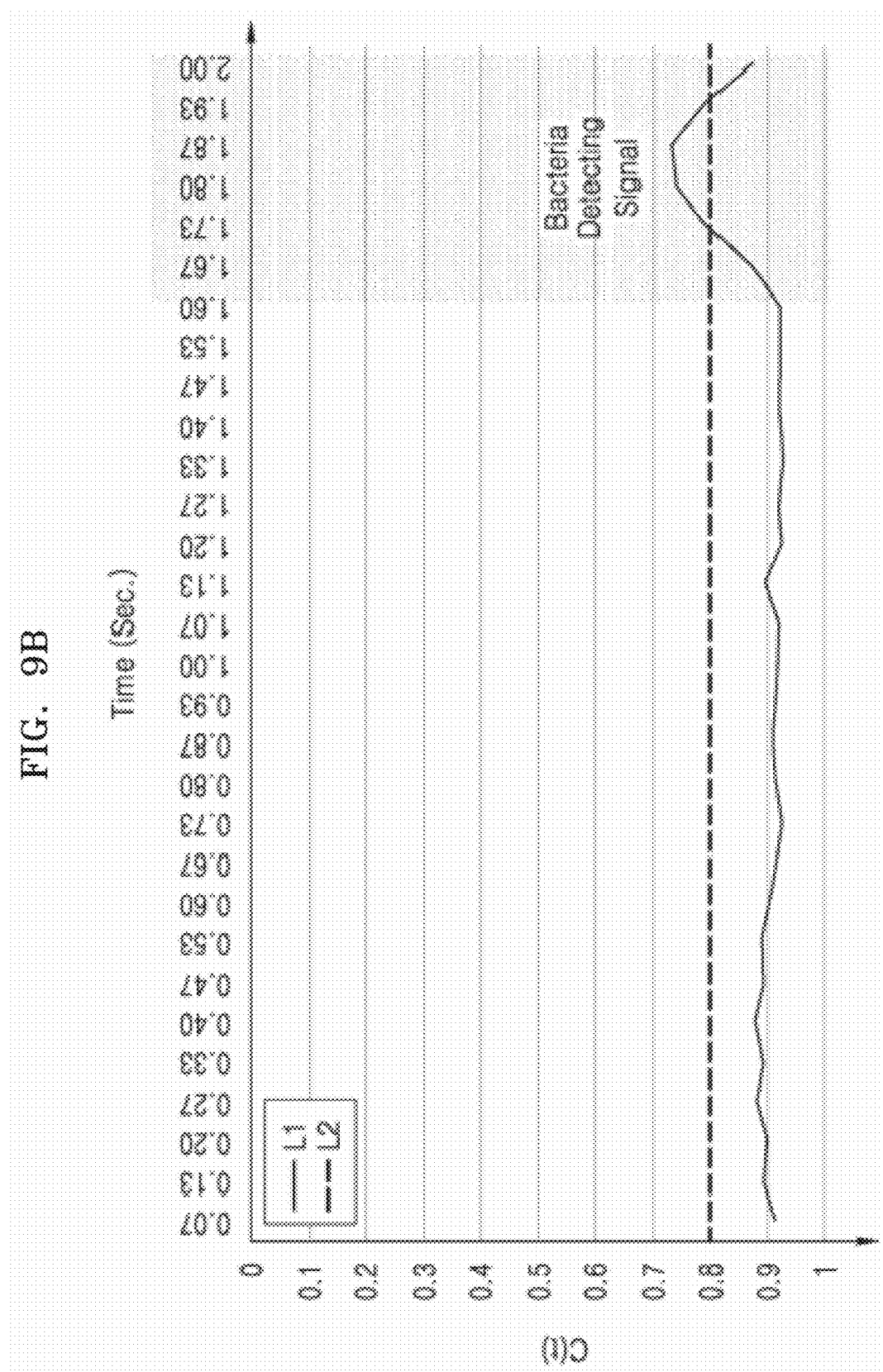
Figure 9C:
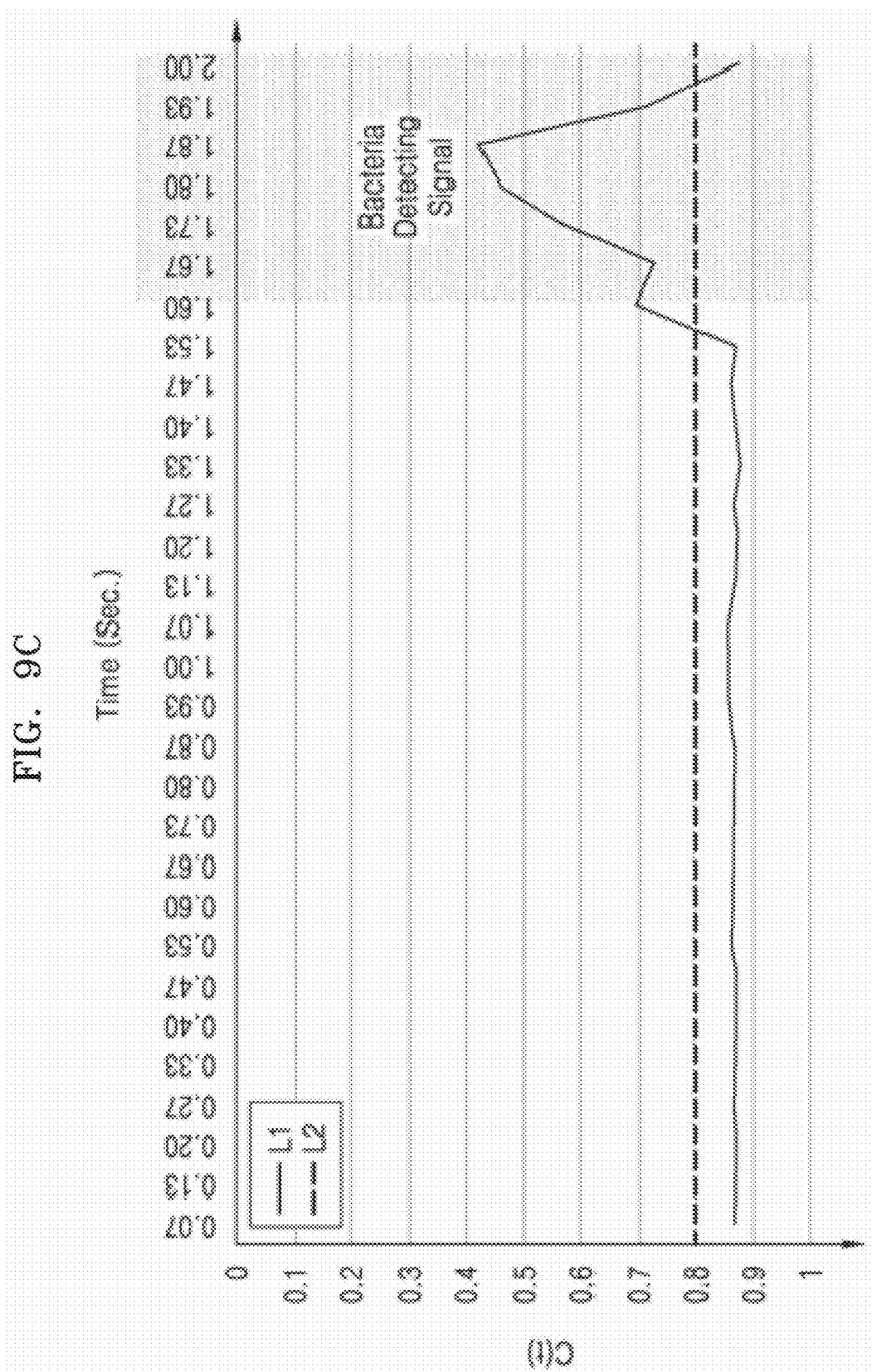

FIGS. 9A to 9C are graphs showing temporal correlation coefficient according to a bacterial concentration in a fluid in the water examination device according to an embodiment of the present disclosure. FIGS. 9A to 9C show changes in the temporal correlation coefficient according to a concentration of microbes, when microbes are artificially injected into the fluid contained in the cup 190.

In the graphs of FIGS. 9A to 9C, an x-axis denotes an axis regarding time (t) and y-axis denotes an axis regarding the temporal correlation coefficient (C(t)). Here, a dashed line L2 denotes a reference value of the temporal correlation coefficient of the laser speckle set in advance in the detector 120. Also, a solid line L1 denotes measurement data of the temporal correlation coefficient of the laser speckle obtained according to time through the detector 120.

The solid line L1 of FIG. 9A denotes the temporal correlation coefficient of the laser speckle obtained by the detector 120, when the microbes are not injected in the fluid.

Referring to FIG. 9A, when there are no microbes in the fluid, there is no change in the laser speckle generated due to the scattering in the fluid, and thus, the temporal correlation coefficient is nearly consistent according to time and may not exceed the reference value L1 set in advance.

The solid line L1 of FIG. 9B denotes the temporal correlation coefficient of the laser speckle obtained by the detector 120 when 4 ml of microbes with a concentration of 10^0 cfu/ml is injected in the fluid. The solid line L1 of FIG. 9C denotes the temporal correlation coefficient of the laser speckle obtained by the detector 120 when 4 ml of microbes with a concentration of 10^1 cfu/ml is injected in the fluid.

Referring to FIGS. 9B and 9C, when there are microbes in the fluid, the laser speckles generated due to the scattering in the fluid change according to time, and thus, the temporal correlation coefficient changes at the time point when the microbes are sensed. In FIGS. 9B and 9C, a shaded region (bacteria detecting signal) denotes the change in the temporal correlation coefficient at the time point of detecting the microbes, and as the concentration of the microbes increases, a peak of the temporal correlation coefficient increases. In addition, in the shaded region of FIGS. 9B and 9C, the detector 120 may determine that there are the microbes when the temporal correlation coefficient (L1) of the laser speckle exceeds the dashed line (L2), that is, the reference value set in advance. Here, when there are microbes, a measurement time taken for the detector 120 to sense the microbes may be a section from a time point when the temporal correlation coefficient rapidly changes and to a point where the temporal correlation coefficient meets the dashed line L2, that is, the reference value, and with reference to FIGS. 9B and 9C, the measurement time may be about 0.2 second or less.

As such, the water examination device according to the embodiments of the present disclosure may sense the microbes that are the impurities in the fluid within a very short time period, e.g., 0.2 sec. or less, that is, in real-time. Also, the water examination device according to the embodiments of the present disclosure may estimate the concentration of the microbes by using the change ratio of the temporal correlation coefficient or the peak value. Also, the water examination device may detect the microbes even when the concentration of the microbes is low (10^0 cfu/ml).

As described above, the water examination device according to the embodiments of the present disclosure may estimate whether there are microbes in the fluid or the concentration of the microbes at low costs, by using the change in the temporal correlation of the laser speckle.

Hereinafter, the method of detecting the microbes in the water examination device according to another embodiment of the present disclosure will be described below. The method of detecting the microbes in the water examination device according to another embodiment of the present disclosure may detect whether there are the microbes in the fluid or the concentration of the microbes by using a spatial correlation, instead of the temporal correlation. Hereinafter, the above method will be described below in more detail.

Figures 10A, 10B, 10C, 10D:
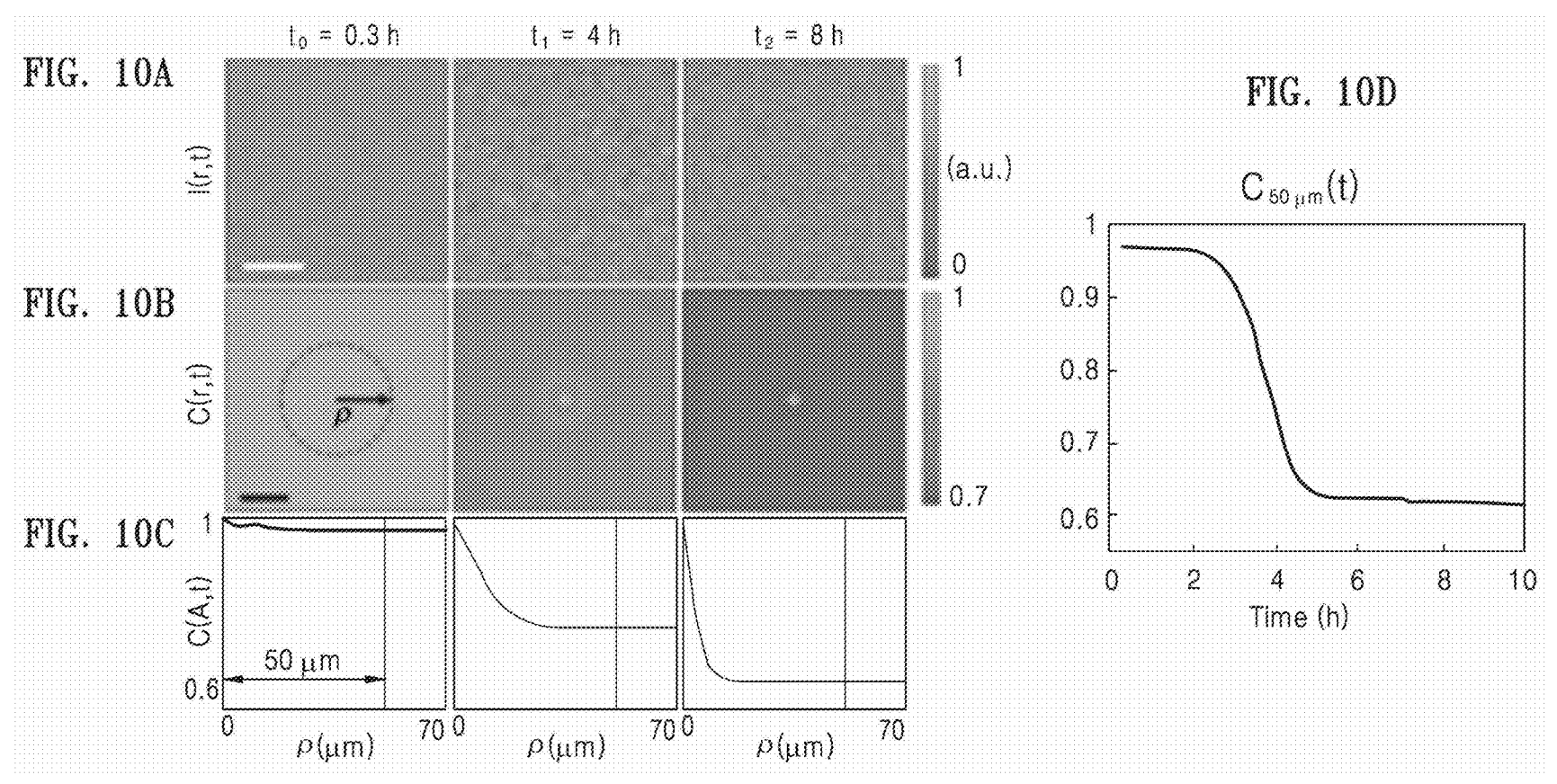

FIGS. 10 and 11 are diagrams for describing a principle of detecting microbes in a water examination device according to another embodiment of the present disclosure.

Referring to FIGS. 10 and 11, the controller 130 is provided with an optical image measured in the time-serial manner from the controller 120, and may determine information about concentration of microbes in the sample from the optical image.

The controller 130 may obtain a spatial correlation of an interference pattern. Here, the spatial correlation expressed by Equation below may indicate how a brightness of an arbitrary pixel and a brightness of a pixel spaced apart from that pixel by a distance r are similar to each other on an image measured at a time t, in a number within a certain range (see (b) of FIG. 11). The certain range may be a range from −1 to 1. That is, the spatial correlation indicates a correlation degree between an arbitrary pixel and another pixel, and 1 denotes a positive correlation, −1 denotes a negative correlation, and 0 denotes no correlation. In particular, because the illuminance is emitted evenly before forming the interference pattern, the spatial correlation of a sample image indicates a positive correlation close to 1. However, after forming the interference pattern, the value of correlation may decrease in the direction toward 0.

The detector 120 may define a brightness measured at time t in a pixel at a location r'=(x,y) as l(r',t), and may define a brightness of a pixel spaced by a distance r as l(r'+r, t). The spatial correlation may be expressed by Equation 5 below by using the above.

$$C(r, t) = \frac{1}{C_0(t)} \int\int I(r' + r, t) I(r', t) dr' \qquad \text{[Equation 5]}$$

$C_0(t)$ is used to set the range of Equation 5 between −1 to 1. When the brightness l(r',t) measured at time t in an arbitrary pixel and the brightness l(r'+r,t) of the pixel spaced by a distance r are equal to each other, the spatial correlation is 1, and the spatial correlation is less than 1 when the above brightnesses are not equal to each other.

In an embodiment, the spatial correlation as described above may be only represented as a function for time. To this end, the controller 130 may calculate an average of the spatial correlation with respect to a pixel having a distance r from an arbitrary pixel and having the same size by using Equation 6 below (see (b) of FIG. 11).

$$C(\rho, t) = \frac{1}{2\pi} \int_0^{2\pi} C(r, t) d\theta \qquad \text{[Equation 6]}$$

In an embodiment, the controller 130 may substitute a distance set in advance in Equation 6 above to represent a function for the time, and may identify a degree of forming the interference pattern as a value within a certain range, e.g., 0 to 1, by using the function (see (d) of FIG. 11).

The controller 130 may distinguish foreign matters from microbes in the sample through a change in the pattern of the sample image according to time. In case of the foreign matters, there is no change in the image according to time, but in case of the microbes, there is a change in the shape, the size, etc. in the image according to time. Thus, the water examination device 100 may distinguish the foreign matters from the microbes.

In addition, the controller 130 may determine information on the concentration of microbes by using the spatial correlation. The spatial correlation may be obtained by generating two identical overlaid images by using one image, shifting one of the two images as much as a distance set in advance in one direction, and analyzing how two adjacent pixels in the shifted image and non-shifted image are similar to each other. Here, the spatial correlation becomes a criterion representing how the image is uniform. When an interference pattern is generated due to a colony, similarity between two adjacent pixels degrades due to small interference patterns, and a value of the spatial correlation also degrades.

The above spatial correlation coefficient varies depending on the shifted distance r (see (b) of FIG. 10), and within a certain distance range, as the shifted distance r increases, the value of the spatial correlation coefficient decreases, and over the certain distance range, the value of the spatial correlation coefficient is nearly consistent. Therefore, in order to obtain more significant spatial correlation, the controller 130 may obtain the spatial correlation by shifting the image by a certain distance set in advance or greater. Here, the certain distance r set in advance is dependent upon a speckle size, and the controller 130 may obtain the spatial correlation by shifting the image as much as a pixel size greater than the speckle size when expressed in units of pixel. For example, the certain distance set in advance may be at least three-pixel distance or greater.

In addition, the controller 130 obtains the temporal correlation of the interference pattern in the sample image, as well as the spatial correlation as above, and may detect the microbes based on the obtained temporal correlation. The controller 130 may calculate the temporal correlation coefficient between images by using information about images of the interference pattern measured in the time-serial manner, and may detect a microbe colony in the sample based on the temporal correlation coefficient.

The controller 130 may detect the microbes through the analysis about decreasing of the calculated temporal correlation coefficient to a reference value set in advance or less.

For the above analysis, the water examination device 100 according to an embodiment of the present disclosure may further include a multiple scattering amplification member for amplifying the number of multiple scattering times of the light incident in the cup 190 in the sample. For example, the multiple scattering amplification member (not shown) is provided on a moving passage of the light between the wave source 110 and the cup 190 or between the cup 190 and the detector 120, and amplifies the number of multiple scattering times of the light. The multiple scattering amplification member (not shown) is attachable to or detachable from the water examination device 100, and may be used as necessary. Through the above configuration, the water examination device according to the embodiments of the present disclosure may detect the microbes in the fluid contained in the cup 190 within a short period of time.

Hereinafter, a water monitoring method according to an embodiment of the present disclosure will be described below. FIG. 12 is a flowchart illustrating a water monitoring method according to an embodiment of the present disclosure.

Figure 12:
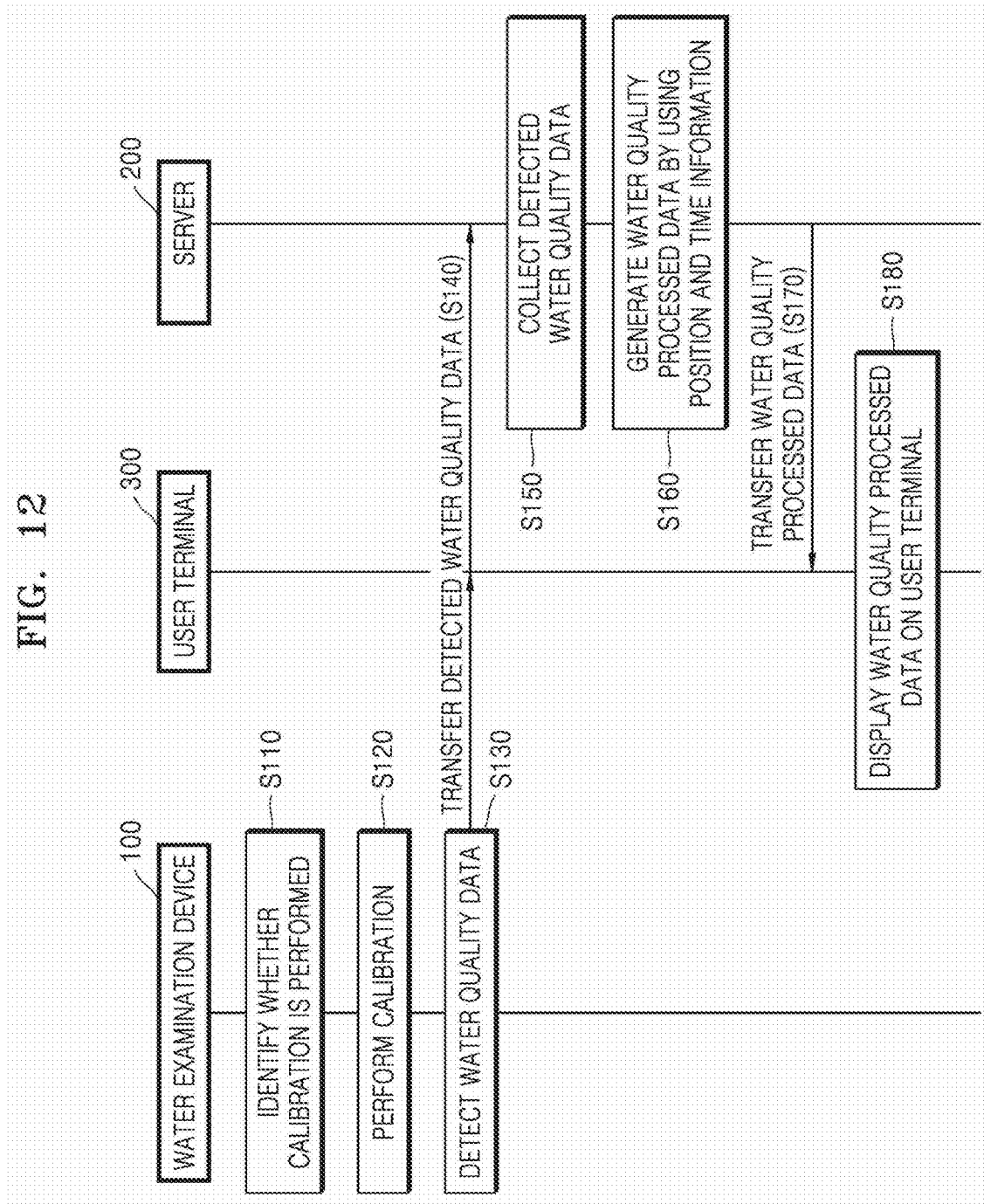
FIG. 12 is a flowchart illustrating a water monitoring method according to an embodiment of the present disclosure.

Referring to FIG. 12, the water monitoring method according to an embodiment of the present disclosure includes: identifying, by the water examination device 100, whether the calibration is made (S110); performing the calibration in the water examination device 100 (S120); detecting water quality data by the water examination device 100 in which the calibration is performed (S130); transferring the detected water quality data from the water examination device 100 to the server 200 (S140); collecting the detected water quality data by the server 200 (S150); generating, by the server 200, water quality processed data by using position and/or time information (S160); transferring the generated water quality processed data from the server 200 to the user terminal 300 (S170); and displaying the water quality processed data on the user terminal 300 (S180).

First, the water examination device 100 identifies whether the calibration is performed (S110). That is, the controller 130 of the water examination device 100 identifies whether the calibration is performed in the water examination device 100, based on whether there is a calibration value stored in advance (for example, a shutter speed value, a voltage at the wave source, etc.).

Next, when the calibration is not performed in the water examination device 100, the water examination device 100 performs a calibration (S120). That is, the calibration unit 180 controls the water examination device 100 in order for the intensity of light measured by the detector 120 to be in a certain range set in advance. This will be described in detail later with reference to FIG. 13.

Next, water quality data is detected from the water examination device 100 in which the calibration is performed (S130). In detail, the detector 120 may detect the laser speckles that are generated when the irradiated waves are multiple scattered in the fluid L, at every preset time point. The detector 120 may detect the laser speckle at a first time point at least, and may detect the laser speckle at a second time point, and then, may provide the controller 130 with the detected laser speckles. The first time point and the second time point are just examples selected for convenience of description, and the detector 120 may detect laser speckles at a plurality of time points more than the first and second time points.

Next, the detected water quality data is transferred from the water examination device 100 to the server 200 via the network 400 (see FIG. 1) (S140). The water quality data is collected by the server 200 (S150).

Next, the server 200 generates water quality processed data by using position and/or time information (S160). In detail, the server 200 may collect water quality data examined by each water examination device 100, processes the water quality data, and provides the water quality data processed as above to the user terminals 300. Here, the water quality data processed by the server 200 and provided to the user terminal 300 may include a water quality level measured by the corresponding user terminal 300 in comparison with a total water quality average, a water quality level in a region where the corresponding user terminal 300 is located in comparison with the total water quality average, a deviation in water quality according to the region, a variation in the water quality according to time, etc.

Next, the generated water quality processed data is transferred from the server 200 to the user terminal 300 via the network 400 (see FIG. 1) (S170). In addition, the water quality processed data is displayed on the user terminal 300 (S180).

Hereinafter, the process of performing the calibration in the water examination device 100 will be described in detail below.

Figure 13:
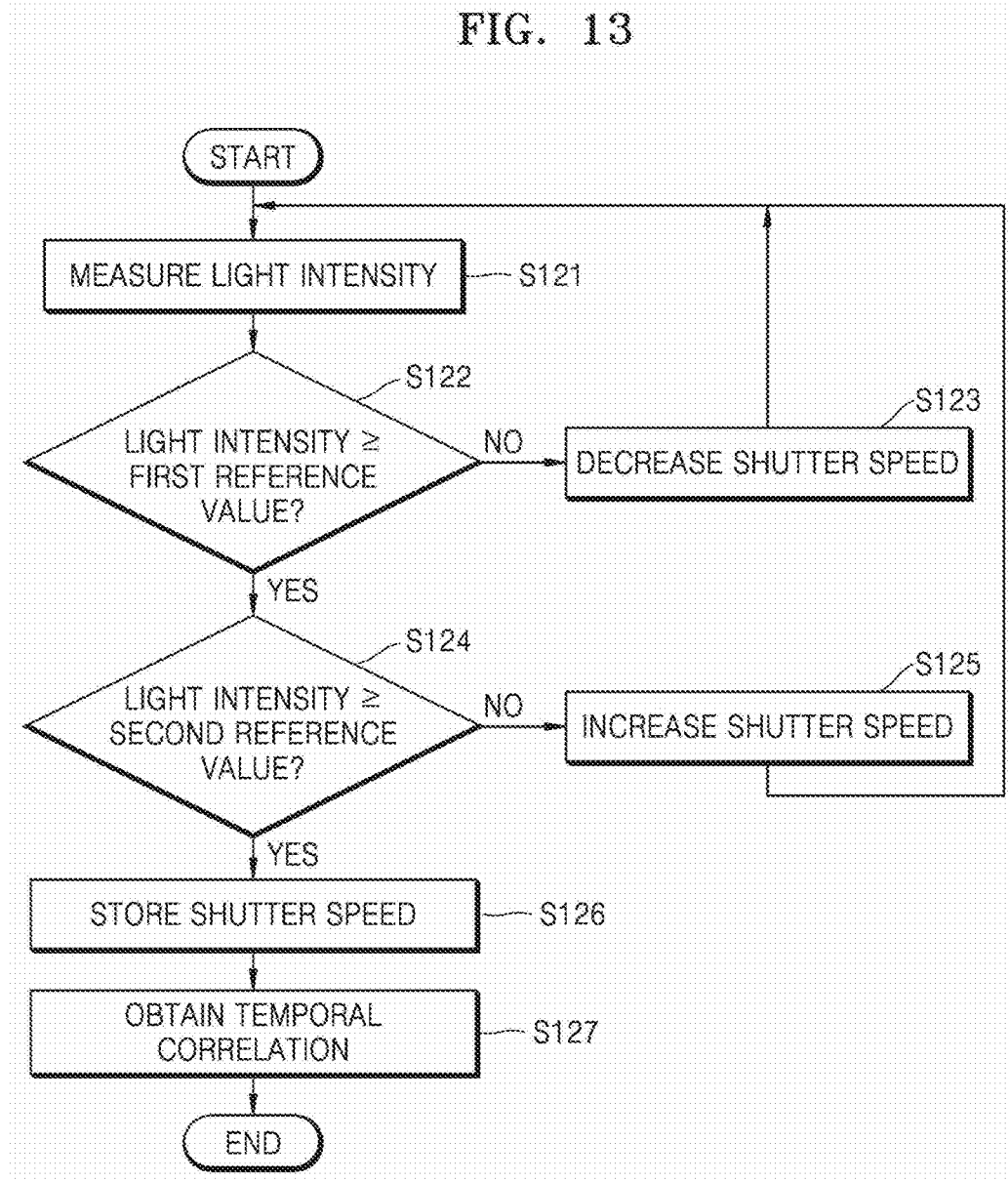
FIG. 13 is a flowchart showing operation S120 in the water monitoring method of FIG. 12 in detail.

FIG. 13 is a flowchart illustrating operation S120 of FIG. 12 in more detail.

Referring to FIG. 13, the method of detecting microbes in the water examination device according to another embodiment of the present disclosure includes: measuring, by the detector 120, the intensity of light that is irradiated from the wave source 110 and passes through the multiple scattering amplification region 165 (S121); determining whether the light intensity measured by the detector 120 is equal to or greater than a first reference value (S122); when the light intensity measured by the detector 120 is not equal to or greater than the first reference value, controlling, by the calibration unit 180, the shutter speed of the shutter 122 to be decreased (S123); when the light intensity measured by the detector 120 is equal to or greater than the first reference value, determining whether the light intensity measured by the detector 120 is equal to or less than a second reference value (S124); when the light intensity measured by the detector 120 is not equal to or less than the second reference value, controlling, by the calibration unit 180, the shutter speed of the shutter 122 to be increased (S125); when the light intensity measured by the detector 120 is equal to or less than the second reference value, storing the current shutter speed (S126); and obtaining, by the controller 130, a temporal correlation of the laser speckle, by using the image detected by the detector 120 (S127).

This will be described below in more detail.

First, the intensity of light irradiated from the wave source 110 and passed through the multiple scattering amplification region 165 is measured by the detector 120 (S121). Here, the process of measuring the light irradiated from the wave source 110 in the detector 120 is described in detail above, and detailed descriptions thereof are omitted.

Next, it is determined whether the light intensity measured by the detector 120 is equal to or greater than the first reference value (S122). Here, a calibration reference value may be determined from an average of intensity values of respective pixels in an image detected by the detector 120.

In detail, in case of an 8-bits image sensor, an intensity of each pixel has a value between 0 to 255, and an intermediate value, that is, 128, may be set as a reference value. In addition, based on various experimental data, an appropriate light intensity range may be set as ±5 from the reference value. In addition, a minimum value of the appropriate light intensity range is set as a first reference value and a maximum value of the appropriate light intensity range may be set as a second reference value.

For example, when the average value of the intensities ranges 123 to 133, it may be set as an appropriate light intensity. (Here, the first reference value may be 123 and the second reference value may be 133.) In addition, an average of the intensity values of the pixels in the image that is irradiated from the wave source 110 and detected by the detector 120 after passing through the multiple scattering amplification region 165 is measured, and when the average of the intensity values is less than the first reference value, e.g., 123, the calibration unit 180 determines that the light intensity is not sufficient and controls the shutter speed of the shutter 122 to be decreased in order to increase the intensity of light incident to the sensor unit 121 (S123).

When the light intensity measured by the detector 120 is equal to or greater than the first reference value, it is determined whether the light intensity measured by the detector 120 is equal to or less than the second reference value (S124).

As a result of determination, when the average of the intensity values of the pixels in the detected image is greater than the second reference value, e.g., 133, the calibration unit 180 determines that the light intensity is excessive and controls the shutter speed of the shutter 122 to be increased in order to decrease the intensity of the light incident to the sensor unit 121 (S125).

In addition, when the light intensity measured by the detector 120 is equal to or less than the second reference value, the current shutter speed is stored (S126).

Last, the controller 130 obtains the temporal correlation of the laser speckle by using the image detected by the detector 120 (S127). Here, the process of obtaining the temporal correlation of the laser speckle is described above in detail, and detailed descriptions thereof are omitted.

As described above, after calibrating the intensity of light detected by the detector 120 within a certain range by using the calibration unit 180, the controller 130 may obtain the temporal correlation of the laser speckle. Thus, even when the performance of the wave source 110 degrades, deterioration such as mosses grown in the detector 120 occurs, or there is a deviation in container containing the fluid sample, an error in obtaining the temporal correlation of the laser speckle may be minimized.

Hereinafter, the water examination device according to another embodiment of the present disclosure will be described below.

Figure 14:
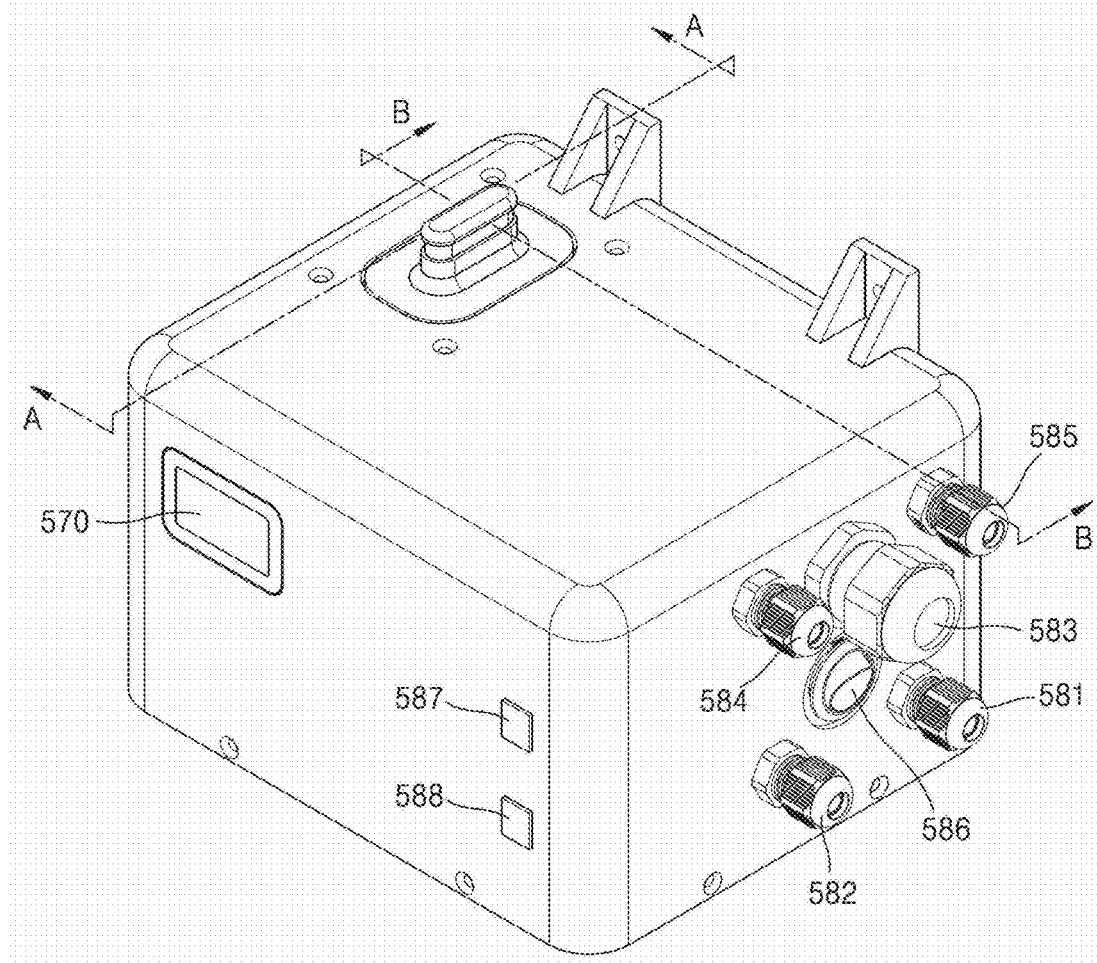
FIG. 14 is a conceptual diagram of a water examination device according to another embodiment of the present disclosure.
Figure 15:
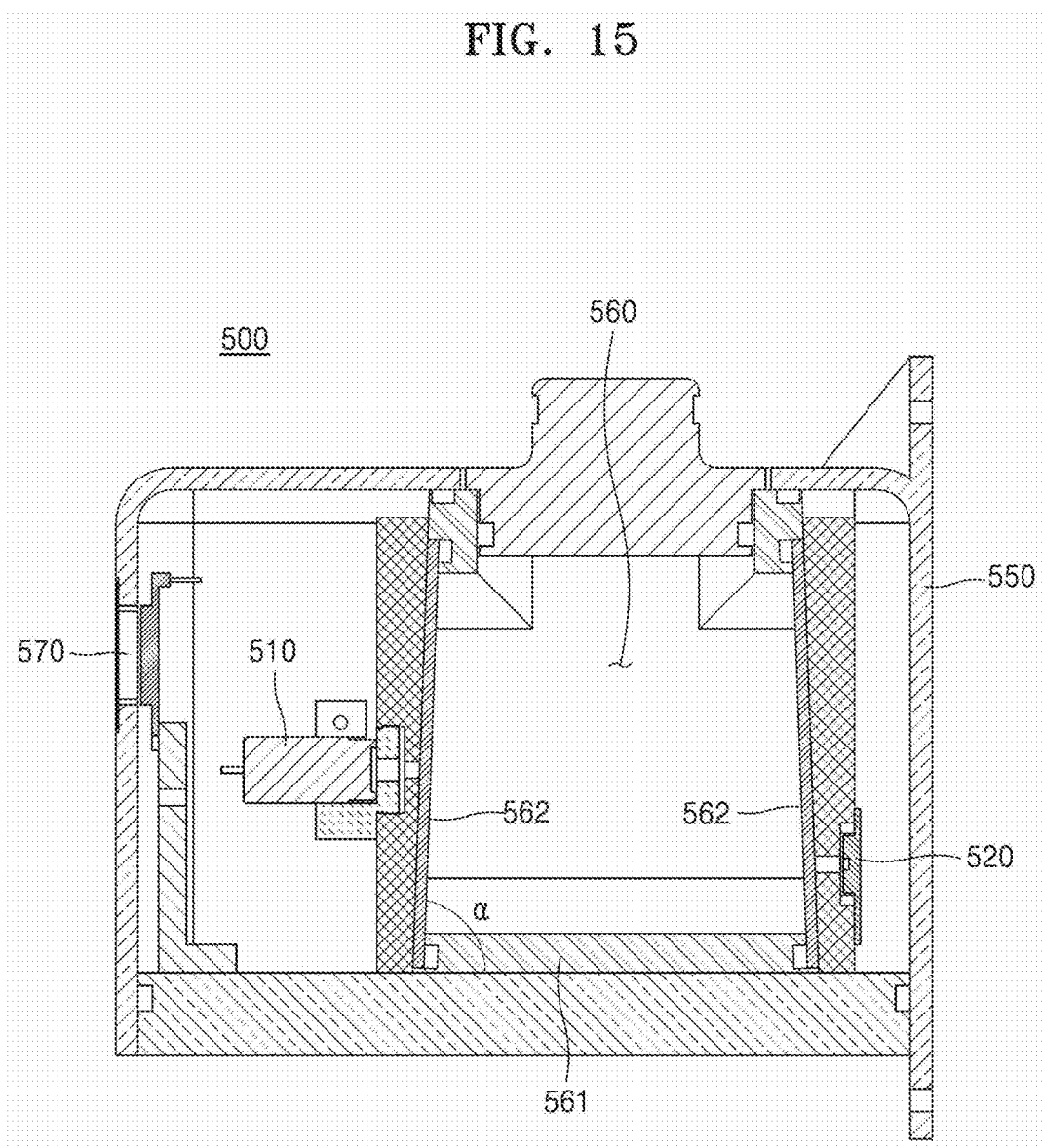
FIG. 15 is a cross-sectional view taken along line A-A of FIG. 14.
Figure 16:
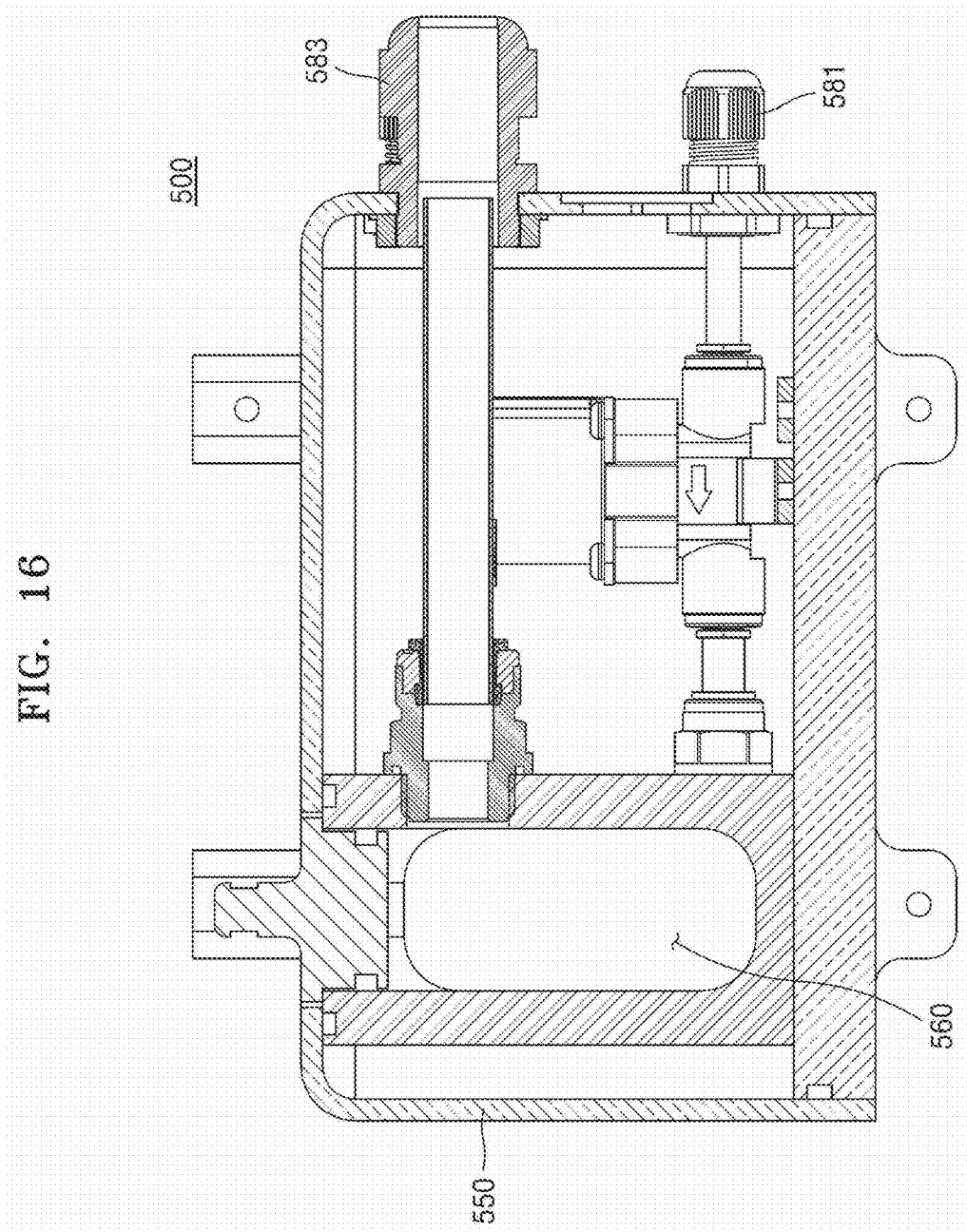
FIG. 16 is a cross-sectional view taken along line B-B of FIG. 14.

FIG. 14 is a conceptual diagram of a water examination device 500 according to another embodiment of the present disclosure, FIG. 15 is a cross-sectional view taken along line A-A of FIG. 14, and FIG. 16 is a cross-sectional view taken alone line B-B of FIG. 14.

Referring to FIGS. 14 to 16, the water examination device 500 according to another embodiment of the present disclosure may include a wave source 510, a detector 520, a main body 550, and a fluid accommodation unit 560. In addition, although not shown in FIGS. 14 to 16, the water examination device 500 may further include the display unit 170 (see FIG. 2), the controller 130 (see FIG. 2), and the alarm unit 140 (see FIG. 2) described above with reference to FIG. 2. Here, the wave source 510 and the detector 520 are described above with reference to FIG. 2, and detailed descriptions thereof are omitted. The water examination device 500 according to another embodiment of the present disclosure may include a kind of turbidity meter.

The main body 550 forms an outer appearance of the water examination device 500, and may include the wave source 510, the detector 520, and the fluid accommodation unit 560 formed therein. Although the main body 550 is formed to have a hexahedral shape in the drawings, but one or more embodiments of the present disclosure are not limited thereto. That is, a size, a shape, and a material of the main body 550, and a position of forming the fluid accommodation unit 560 in the main body 550 may be changed variously.

The fluid accommodation unit 560 may have an empty box shape so as to accommodate a fluid therein. Here, the fluid accommodation unit 560 may include a kind of water tank. The fluid accommodation unit 560 may include a bottom portion 561 and wall portions 562. In other words, the fluid accommodation unit 560 may be formed by the bottom portion 561 and the wall portions 562.

The bottom portion 561 forms a bottom surface of the fluid accommodation unit 560 and has a flat surface. The bottom portion 561 may at least partially include a multiple scattering amplification region 565 described above.

In addition, the wall portions 562 are formed in an approximately perpendicular direction from the bottom portion 561. The multiple scattering amplification region 565 and/or a reflective region 567 described above may be formed in at least a part of the wall portion 562.

Here, in the water examination device 500 according to an embodiment of the present disclosure, an angle ($\alpha$) between the wall portion 562 and the bottom portion 561 is not a right angle, but is slightly inclined (that is, oblique).

In detail, during the light scattering due to the laser reflection in the water examination device 500 according to an embodiment of the present disclosure, some of the scattered light is exposed to outside, and there is a loss in the intensity of light received by the detector 120 (see FIG. 1), and thus, the loss of light intensity affects the result obtained through the light scattering analysis.

To address the above issue, according to one embodiment of the present disclosure, the angle (α) formed by the wall portion 562 and the bottom portion 561 is not the right angle, but is slightly inclined. That is, the wall portion 562 is formed such that the angle (α) formed by the wall portion 562 and the bottom portion 561 is about 85° to 88°, and thus, the laser reflected by the wall portion 562 proceeds toward a side opposite to the opened surface to reduce the loss of light intensity. Therefore, the light scattering effect may be improved.

In other words, the wall portion 562 may be formed to have a narrowed entrance in an upward direction (that is, in a +z direction), or may have a diameter that is gradually reduced upward. According to the present disclosure, the loss of light emitted from the wave source 510 is reduced, and the light scattering effect may be improved.

In addition, the water examination device 500 according to another embodiment of the present disclosure may further include a water inlet pipe 581, a water outlet pipe 582, a second water outlet pipe 583, a power supply unit 584, a data output unit 585, a power switch 586, a measurement button unit 587, and a calibration button unit 588.

The water inlet pipe 581 supplies a fluid into the fluid accommodation unit 560.

The water outlet pipe 582 discharges the fluid in the fluid accommodation unit 560 to outside.

Here, in the water examination device 500 according to another embodiment of the present disclosure, an additional fluid accommodation unit for removing bubbles is not provided, and instead, the fluid is injected to and discharged from the fluid accommodation unit 560 regularly (e.g., once per minute), and thus, a function for removing dissolved oxygen from the fluid is performed.

To this end, the water inlet pipe 581 and the water outlet pipe 582 are arranged at a lower end of the fluid accommodation unit 560, but a discharge port may be lower than an injection port. Here, although the water inlet pipe 581 and the water outlet pipe 582 are at the same height in the drawings, one or more embodiments of the present disclosure are not limited thereto, that is, the water outlet pipe 582 may be at the same height as or lower than the water inlet pipe 581. As described above, when the height of the water outlet pipe 582 is set to be equal to or lower than that of the water inlet pipe 581, the fluid in the fluid accommodation unit 560 may be sufficiently discharged.

Moreover, in order to prevent overflow from the water inlet pipe 581 and the water outlet pipe 582, a second water outlet pipe 583 may be additionally arranged at a height that is greater than those of the water inlet pipe 581 and the water outlet pipe 582. Here, a fluid discharging capacity per unit time of the second water outlet pipe 583 may be greater than that of the water outlet pipe 582.

The power supply unit 584 may be connected to an external power to supply the external power to the water examination device 500. In addition, the power switch 586 may open/close the power supply to the power supply unit 584.

The data output unit 585 may be connected to an external electronic device (an external terminal (see 300 of FIG. 1) or the server 200 (see FIG. 1)), and may output measurement data of the water examination device 500 to the outside.

The measurement button unit 587 may turn on/off the turbidity measurement function of the water examination device 500.

The calibration button unit 588 may turn on/off the calibration function. Here, the calibration function may denote a function of injecting a reference material, a measurement value of which is already known, in the fluid accommodation unit 560 regularly (e.g., every two years) and, when a data deviation of the reference material is generated, calibrating the data deviation.

As described above, in the water examination device 500 according to the embodiment of the present disclosure, an additional fluid accommodation unit for removing bubbles is not provided, and instead, the fluid is injected to and discharged from the fluid accommodation unit 560 regularly (e.g., once per minute), and thus, a function for removing dissolved oxygen from the fluid is performed. In addition, by removing the dissolved oxygen by the above method, a speed and accuracy of the measurement may be improved.

The turbidity may be measured by using the water examination device 500 according to an embodiment of the present disclosure as follows.

When the power switch 586 is pushed, an initial cleaning is performed while waiting a certain time period (e.g., 3 minutes).

Next, when the measurement button unit 587 is pushed, the measurement is repeatedly performed automatically with a certain time interval (e.g., 1 minute interval). This will be described in more detail as follows.

First, while the water inlet pipe 581 is opened and the water outlet pipe 582 is closed, the fluid is introduced into the fluid accommodation unit 560 through the water inlet pipe 581 and is completely filled in the fluid accommodation unit 560.

Next, while the water inlet pipe 581 is closed and the water outlet pipe 582 is closed, the turbidity is measured. That is, the wave irradiated from the wave source 510 is multiple scattered in the fluid L, and then, is detected by the detector 520 to perform the measurement.

Next, when the measurement is finished, the water inlet pipe 581 is closed and the water inlet pipe 582 is opened, and thus, the fluid in the fluid accommodation unit 560 is discharged to outside.

Then, while the water inlet pipe 581 is opened and the water outlet pipe 582 is opened, the fluid is introduced into the fluid accommodation unit 560 to perform the cleaning.

The above processes are repeatedly performed and the turbidity of the fluid is measured. As described above, when the turbidity is measured by using the water examination device 500 according to the present disclosure, the rapid measurement may be performed in real-time as compared with an existing turbidity meter, and it is easy to maintain the turbidity meter.

Although not shown in the drawings, the water examination device according to another embodiment of the present disclosure may include a water quality meter. The above water examination device may be installed on a water system, and water quality of the water system may be analyzed in real-time. That is, the water examination device according to another embodiment of the present disclosure may measure a flow rate of the fluid flowing in the water system, and the flow amount may be analyzed by using the flow rate and a cross-sectional area of a pipe. In addition, when the flow rate measured as above is consistent, the water examination device (that is, the water quality meter) is operated to measure the water quality, and the measurement data may be transferred to the server 200 (see FIG. 1), the user terminal 300 (see FIG. 1), etc.

While the present disclosure has been particularly shown and described with reference to preferred embodiments thereof, it will be understood by those skilled in the art that various changes in form and details may be made therein without departing from the spirit and scope of the present disclosure as defined by the appended claims. The preferred embodiments should be considered in descriptive sense only and not for purposes of limitation. Therefore, the scope of the present disclosure is defined not by the detailed description of the disclosure but by the appended claims, and all differences within the scope will be construed as being included in the present disclosure.

According to the water examination device and the water monitoring system using the water examination device in the embodiments of the present disclosure, changes in the temporal correlation or the spatial correlation of the laser speckles are used to estimate whether there are the impurities including microbes in the fluid and/or the concentration of the impurities rapidly at low costs, and the water quality may be examined.

It should be understood that embodiments described herein should be considered in a descriptive sense only and not for purposes of limitation. Descriptions of features or aspects within each embodiment should typically be considered as available for other similar features or aspects in other embodiments. While one or more embodiments have been described with reference to the figures, it will be understood by those of ordinary skill in the art that various changes in form and details may be made therein without departing from the spirit and scope as defined by the following claims.

What is claimed is:

1. A water examination device comprising:
a main body;
a fluid accommodation unit formed in the main body;
a wave source for irradiating waves toward the fluid accommodation unit;
a detector for detecting a laser speckle at every set time period that is set in advance, the laser speckle being generated due to multiple scattering of the waves in the fluid;
a controller for estimating existence of impurities in the fluid by using the detected laser speckle; and
a calibration unit for controlling the wave source or the detector such that an intensity of light irradiated from the wave source and measured by the detector is within a certain range set in advance,
wherein the fluid accommodation unit includes:
a bottom portion formed in the main body; and
a wall portion formed to have a certain angle with respect to the bottom portion and includes a reflective region,
wherein an angle between the bottom portion and the wall portion is not a right angle,
wherein the wall portions facing each other are inclined with respect to the bottom portion toward each other,
wherein the wave source irradiates waves toward the wall portions, and
wherein the fluid accommodation unit is configured to accept a cup of fluid that is separatable from the fluid accommodation unit.

2. The water examination device of claim 1, wherein the detector includes a sensor unit and a shutter formed at one side of the sensor unit to block the light incident in the sensor unit, and
the calibration unit controls a shutter speed of the shutter.

3. The water examination device of claim 2, wherein a calibration reference value of the calibration unit is based on
an average of intensity values of respective pixels in an image detected by the detector.

4. The water examination device of claim 2, wherein, when an intensity of light detected by the detector is equal to or less than a first reference value,
the calibration unit is configured to control the shutter speed of the shutter to be decreased in order to increase the intensity of the light that is incident in the sensor unit.

5. The water examination device of claim 2, wherein, when an intensity of light detected by the detector is equal to or greater than a second reference value,
the calibration unit is configured to control the shutter speed of the shutter to be increased in order to decrease the intensity of the light that is incident in the sensor unit.

6. The water examination device of claim 1, wherein, when an intensity of light detected by the detector is equal to or less than a first reference value,
the calibration unit is configured to increase a voltage at the wave source in order to increase the intensity of the light that is incident in the detector.

7. The water examination device of claim 1, wherein, when an intensity of light detected by the detector is equal to or greater than a second reference value,
the calibration unit is configured to decrease a voltage at the wave source in order to decrease the intensity of the light that is incident in the detector.

8. The water examination device of claim 1, wherein, after calibration of the intensity of light detected by the detector to be within a certain range is performed by the calibration unit,
the controller is configured to estimate existence of impurities in the fluid by using the laser speckle.

9. The water examination device of claim 1, further comprising:
a water inlet pipe connected to the fluid accommodation unit to supply a fluid to the fluid accommodation unit; and
a water outlet pipe connected to the fluid accommodation unit to discharge the fluid from the fluid accommodation unit to outside.

10. The water examination device of claim 9, wherein dissolved oxygen existing in the fluid is removed by regularly supplying the fluid to the fluid accommodation unit via the water inlet pipe and discharging the fluid from the fluid accommodation unit via the water outlet pipe.

11. The water examination device of claim 1, wherein the bottom portion or the wall portion includes a multiple scattering amplification region for amplifying the number of multiple scattering times of the wave irradiated from the wave source in the fluid.

12. The water examination device of claim 11, wherein the multiple scattering amplification region amplifies the number of multiple scattering times of the wave in the fluid by reflecting at least some of the wave irradiated from the fluid toward the fluid.

13. The water examination device of claim 1, wherein the controller obtains a temporal correlation of the detected laser speckle by using the detected laser speckle, and estimates existence of impurities in the fluid in real-time based on the temporal correlation.

14. The water examination device of claim 13, wherein the temporal correlation includes a difference between first image information of the laser speckle detected at a first time point and second image information of the laser speckle detected at a second time point that is different from the first time point.

15. The water examination device of claim 14, wherein the first image information and the second image information comprise at least one of pattern information of the laser speckle and intensity information of the wave.

16. The water examination device of claim 1, wherein the controller obtains a spatial correlation of an interference pattern in an optical image detected by the detector and determines existence of impurities in the fluid based on a change in the spatial correlation of the interference pattern according to time.

* * * * *